US007899689B1

(12) United States Patent
Wizig

(10) Patent No.: US 7,899,689 B1
(45) Date of Patent: *Mar. 1, 2011

(54) METHOD AND SYSTEM FOR PROVIDING A USER-SELECTED HEALTHCARE SERVICES PACKAGE AND HEALTHCARE SERVICES PANEL CUSTOMIZED BASED ON A USER'S SELECTIONS

(75) Inventor: Lewis Howard Wizig, Leawood, KS (US)

(73) Assignee: Vivius, Inc., Leawood, KS (US)

( * ) Notice: Subject to any disclaimer, the term of this patent is extended or adjusted under 35 U.S.C. 154(b) by 1252 days.

This patent is subject to a terminal disclaimer.

(21) Appl. No.: 10/808,810

(22) Filed: Mar. 25, 2004

Related U.S. Application Data

(63) Continuation of application No. 09/434,271, filed on Nov. 4, 1999, now Pat. No. 6,735,569.

(51) Int. Cl.
*G06Q 40/00* (2006.01)
*G06Q 50/00* (2006.01)
*G06Q 10/00* (2006.01)

(52) U.S. Cl. ................. 705/4; 705/2; 705/322
(58) Field of Classification Search ............ 705/2–3, 705/4
See application file for complete search history.

(56) References Cited

U.S. PATENT DOCUMENTS 4,567,359 A   1/1986   Lockwood
4,648,037 A   3/1987   Valentino (Continued)

FOREIGN PATENT DOCUMENTS

JP   59099569 A   6/1984

OTHER PUBLICATIONS

O'Hara, Colleen ; "Comparison shop for health plans online;" Federal Computer Week; Mar. 22, 1999; vol. 13, No. 7; p. 27.*

(Continued)

*Primary Examiner*—Robert W Morgan
*Assistant Examiner*—Rachel L Porter
(74) *Attorney, Agent, or Firm*—Walter G. Hanchuk; Chadbourne & Parke LLP

(57) ABSTRACT

A method and system for allowing a user to select a healthcare services package is disclosed where a central server generally receives personal information data from the user over the Internet regarding the user's preferences with respect to healthcare service providers and the user's sponsor, i.e., the party responsible for paying for all or part of the user's healthcare costs (such as an employer, an insurance company or the user himself). The server thereafter provides a list comprising a plurality of healthcare service providers and information regarding the healthcare service providers (e.g., specialty, rate, location, hospital affiliation, etc.) to the user for selection by the user of a healthcare services panel. Once the server has received the selected healthcare services panel from the user comprising at least one of the listed healthcare service providers, the server determines a healthcare services package and provides the determined healthcare services package to the user for selection by the user. The method and system also provides for registration with the server by healthcare service providers that are interested in being listed for selection by the user, wherein the healthcare service providers are paid according to their registered rates.

12 Claims, 67 Drawing Sheets

U.S. PATENT DOCUMENTS

| | | | |
|---|---|---|---|
| 4,831,526 A | 5/1989 | Luchs et al. | |
| 4,837,693 A | 6/1989 | Schotz | |
| 4,916,611 A | 4/1990 | Doyle, Jr. et al. | |
| 5,070,452 A | 12/1991 | Doyle, Jr. et al. | |
| 5,136,502 A | 8/1992 | Van Remortel | |
| 5,235,507 A | 8/1993 | Sackler et al. | |
| 5,301,105 A | 4/1994 | Cummings et al. | |
| 5,519,607 A * | 5/1996 | Tawil | 705/2 |
| 5,523,942 A | 6/1996 | Tyler et al. | |
| 5,537,315 A | 7/1996 | Mitcham | |
| 5,592,375 A | 1/1997 | Salmon et al. | |
| 5,644,778 A | 7/1997 | Burks | |
| 5,671,276 A | 9/1997 | Eyer et al. | |
| 5,845,256 A | 12/1998 | Pescitelli et al. | |
| 5,873,071 A | 2/1999 | Ferstenberg et al. | |
| 5,878,400 A | 3/1999 | Carter | |
| 5,890,129 A | 3/1999 | Spurgeon | |
| 5,897,622 A | 4/1999 | Blinn et al. | |
| 5,911,687 A * | 6/1999 | Sato et al. | 600/300 |
| 5,915,241 A | 6/1999 | Giannini | |
| 5,918,208 A | 6/1999 | Javitt | |
| 5,926,817 A | 7/1999 | Christeson et al. | |
| 5,930,759 A | 7/1999 | Moore et al. | |
| 5,933,811 A | 8/1999 | Angles et al. | |
| 5,937,392 A | 8/1999 | Alberts | |
| 6,014,629 A * | 1/2000 | DeBruin-Ashton | 705/2 |
| 6,026,364 A | 2/2000 | Whitworth | |
| 6,044,352 A | 3/2000 | Deavers | |
| 6,061,657 A | 5/2000 | Whiting-O'Keefe | |
| 6,067,522 A | 5/2000 | Warady et al. | |
| 6,078,890 A | 6/2000 | Mangin et al. | |
| 6,088,677 A | 7/2000 | Spurgeon | |
| 6,092,047 A | 7/2000 | Hyman et al. | |
| 6,208,973 B1 | 3/2001 | Boyer et al. | |
| 6,208,974 B1 * | 3/2001 | Campbell et al. | 705/3 |
| 6,341,265 B1 | 1/2002 | Provost et al. | |
| 6,343,271 B1 | 1/2002 | Peterson et al. | |
| 6,401,079 B1 | 6/2002 | Kah et al. | |
| 6,488,205 B1 | 12/2002 | Jacobson | |
| 2001/0027403 A1 | 10/2001 | Peterson et al. | |
| 2001/0034618 A1 | 10/2001 | Kessler et al. | |
| 2001/0034621 A1 | 10/2001 | Kirsh et al. | |
| 2002/0010594 A1 | 1/2002 | Levine | |
| 2002/0019754 A1 | 2/2002 | Peterson et al. | |
| 2002/0026334 A1 | 2/2002 | Igoe | |
| 2002/0049617 A1 | 4/2002 | Lencki et al. | |
| 2002/0077869 A1 | 6/2002 | Doyle et al. | |
| 2002/0087364 A1 | 7/2002 | Lerner et al. | |
| 2002/0087444 A1 | 7/2002 | DiPiero et al. | |
| 2002/0091549 A1 | 7/2002 | Provost et al. | |
| 2002/0103672 A1 | 8/2002 | Torres et al. | |
| 2002/0103678 A1 | 8/2002 | Burkhalter et al. | |
| 2002/0123907 A1 | 9/2002 | Strayer | |
| 2002/0128877 A1 | 9/2002 | Levit | |
| 2002/0128879 A1 | 9/2002 | Spears | |
| 2002/0147617 A1 | 10/2002 | Schoenbaum et al. | |
| 2002/0169955 A1 | 11/2002 | Bryany, Jr. et al. | |
| 2002/0198741 A1 | 12/2002 | Randazzo | |
| 2003/0009355 A1 | 1/2003 | Gupta | |
| 2003/0014280 A1 | 1/2003 | Jilinskaia et al. | |
| 2003/0069754 A1 | 4/2003 | Weeks | |
| 2003/0083906 A1 | 5/2003 | Howell et al. | |
| 2003/0120511 A1 | 6/2003 | Legnini | |
| 2003/0187694 A1 | 10/2003 | Rowen | |
| 2003/0187695 A1 | 10/2003 | Drennan | |
| 2003/0191665 A1 | 10/2003 | Fitzgerald et al. | |
| 2003/0191667 A1 | 10/2003 | Fitzgerald et al. | |
| 2003/0191669 A1 | 10/2003 | Fitzgerald | |
| 2003/0195769 A1 | 10/2003 | Francis et al. | |
| 2003/0195771 A1 | 10/2003 | Fitzgerald et al. | |
| 2003/0195773 A1 | 10/2003 | Mahaffey | |
| 2003/0208379 A1 | 11/2003 | Haskey et al. | |
| 2003/0216946 A1 | 11/2003 | Ferraro | |
| 2003/0229516 A1 | 12/2003 | Nickerson | |
| 2004/0002924 A1 | 1/2004 | Boone et al. | |
| 2004/0078247 A1 | 4/2004 | Rowe, III et al. | |
| 2004/0103002 A1 | 5/2004 | Colley et al. | |
| 2008/0040149 A1 * | 2/2008 | Joao | 705/1 |

OTHER PUBLICATIONS

Johnson, Helen, "menu of Options on Offer as Companies and Government Pass Planning to the Individual Tailored Health Benefits on Way", Dec. 20, 1998, South China Morning Post, p. 10.

Schachner, Michael; "Employers prescribe cure for rising drug costs: Formularies, generic alternatives help control costs;" Mar. 21, 1994, Business Insurance, p. 11, 3 pages.

Johnstone, Helen; "Menu of options on offer as companies and government pass planning to the individual Tailored health benefits on way;" Dec. 20, 1998, South China Morning Post, p. 10, 3 pages.

US 5,884,318, 03/1999, Nielsen et al. (withdrawn)

* cited by examiner

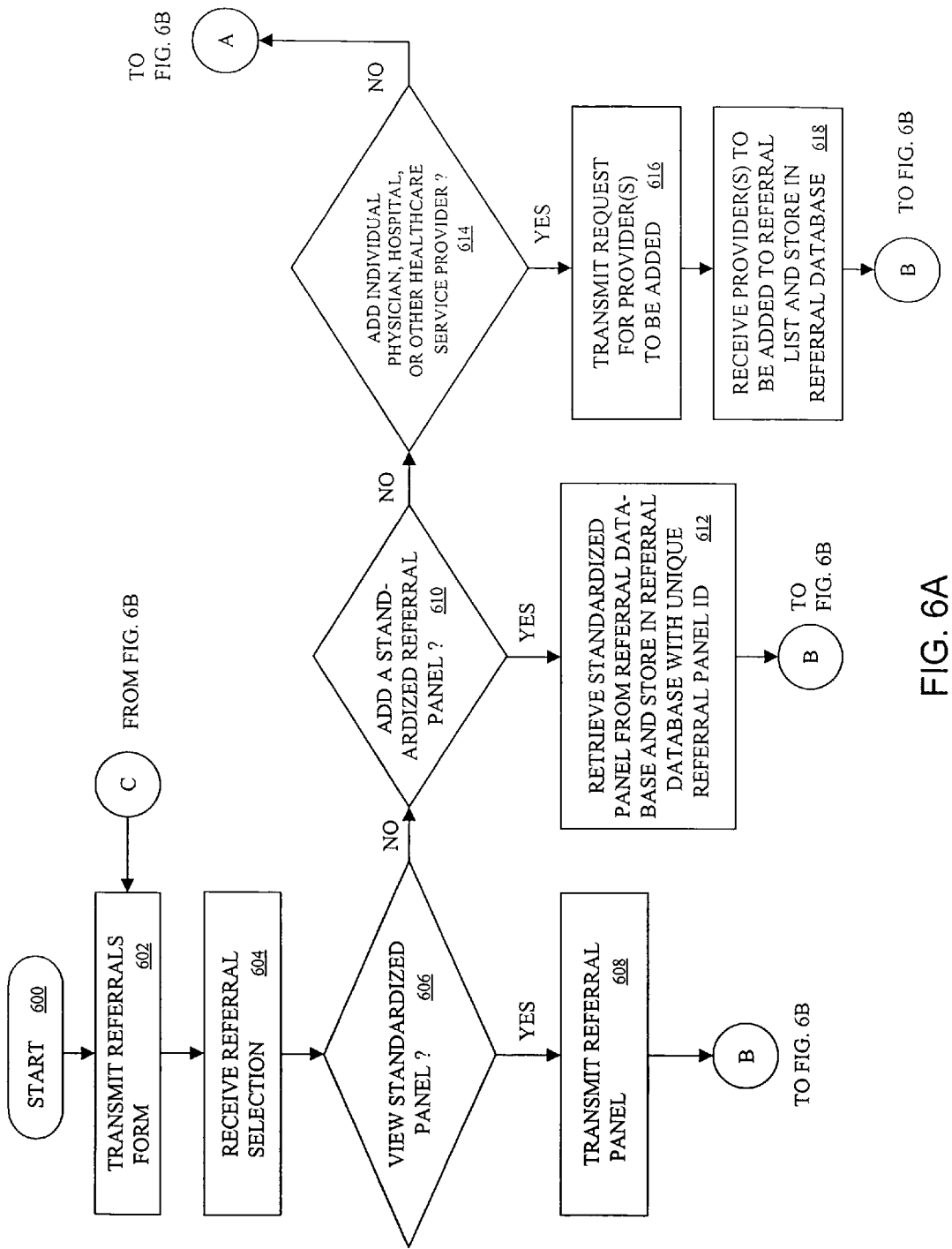

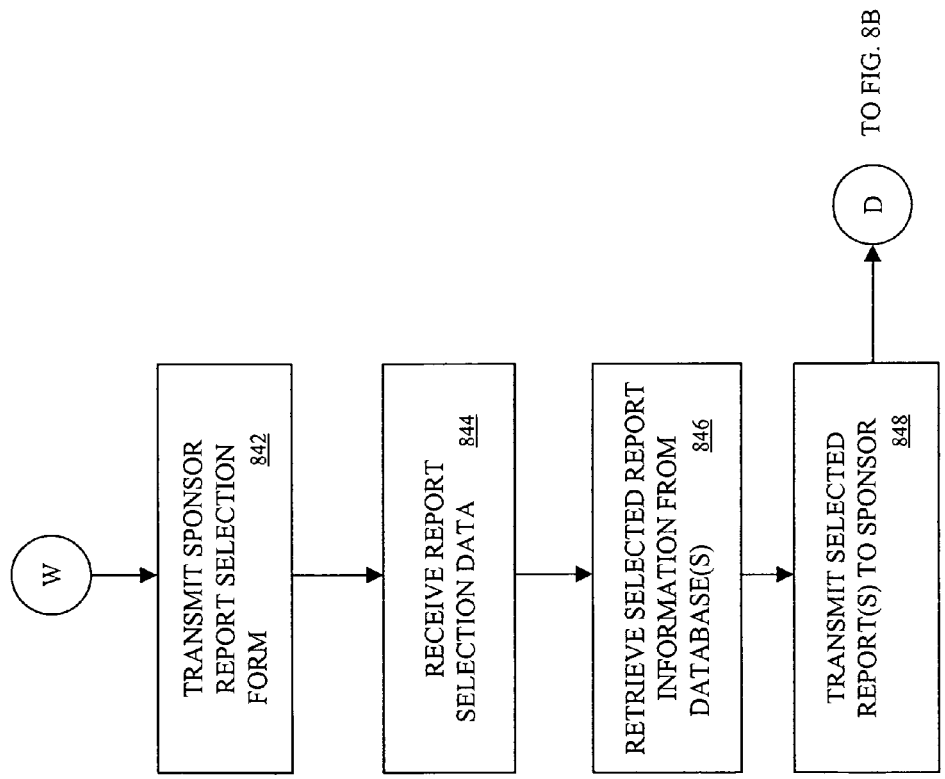

MEMBER PANEL DATABASE 900

| MEMBER ID 905 | NAME (First / Middle / Last) 907 | PANEL ID 908 | CATEGORY 910 | PROVIDER ID 915 | CO-PAYMENT 920 | RATE TYPE - PRE-PAID/FFS (P/F) 923 | RATE 925 | BEGINNING EFFECTIVE DATE (MM/DD/YYYY) 930 | ENDING EFFECTIVE DATE (MM/DD/YYYY) 935 |
|---|---|---|---|---|---|---|---|---|---|
| 1001 | Jenny / Lee / Jones | 2002 | Primary Care Internal Medicine | 87654321 | $ 20 | P | $ 60 | 11/01/1999 | 10/31/2000 |
| 1001 | Jenny / Lee / Jones | 2002 | Dentist | 86003201 | $ 20 | P | $ 8.95 | 11/01/1999 | 10/31/2000 |
| 1001 | Jenny / Lee / Jones | 2002 | Opthamology | 31733258 | $ 20 | P | $ 4.27 | 11/01/1999 | 10/31/2000 |

(rows labeled 950, 960, 970)

FIG. 9

REGISTRATION DATABASE 1000

| LOG-IN IDENTIFIER 1005 | PASSWORD 1010 | COOKIE? (Y/N) 1015 | E-MAIL ADDRESS 1020 | HOME ZIP CODE 1025 | CATEGORIZATION (U/HP/S) 1030 |
|---|---|---|---|---|---|
| john_jones | cubsfan | Y | jjones@email.com | 60201 | U |
| patch_adams | drfunny | N | patch@barnes.com | 63112 | HP |
| robert_m_blind | policy | N | robmblind@tinsurance.com | 60666 | S |
| little_boo | toothman | Y | lilboo@abcdental.com | 53402 | HP |
| john_anderson | jayhawk | N | anderj@hotmail.com | 10019 | HP |
| mifune_go | need4speed | Y | speed@racecox.com | 46224 | S |
| wizigco | inventor | Y | wizig@aol.com | 66211 | S |
| cut_up | stlrams#1 | N | butcher@barnes.com | 63112 | HP |
| slow-hand | longhorn | N | akers@barnes.com | 63112 | HP |

SPONSOREE DATABASE 1100

| LOG-IN IDENTIFIER 1105 | ZIP CODE 1110 | SPONSOR TYPE (U/E/H) 1115 | SPONSOR ID CODE 1120 | SPONSOREE ID CODE 1125 | # ON ACCOUNT 1130 | SPONSOREE BUDGET 1140 |
|---|---|---|---|---|---|---|
| john_jones | 66211 | E | Wizig & Company | 3452112 | 3 | 5000 |
| sandra_smith | 66209 | H | Tifosi Life Co. | 397876 | 1 | 5000 |
| jack_horner | 60609 | H | Tifosi Life Co. | 6216110 | 2 | 5000 |

MEMBER DEMOGRAPHICS DATABASE 1200

| LOG-IN IDENTIFIER 1205 | NAME (First / Middle / Last) 1210 | MEMBER ID 1211 | PANEL ID 1213 | DOB (MM/DD/YYYY) 1215 | SSN 1220 | RELATION 1225 | GENDER (M/F) 1230 | SPONSOREE ID 1240 | |
|---|---|---|---|---|---|---|---|---|---|
| john_jones | John / Michael / Jones | 1000 | 2000 | 06/12/1963 | 123457899 | SELF | M | 3452112 | 1250 |
| john_jones | Jenny / Lee / Jones | 1001 | 2002 | 08/18/1964 | 123457991 | SPOUSE | F | 3452112 | 1260 |
| john_jones | Julia / Lynn / Jones | 1002 | 2007 | 04/13/1992 | 123457992 | CHILD | F | 3452112 | 1270 |

FIG. 12

HEALTHCARE SERVICE PROVIDER DATABASE 1300

| LOG-IN IDENTIFIER 1305 | CATEGORY 1310 | SERVICE TYPE 1315 | PROVIDER ID 1320 | BEGINNING EFFECTIVE DATE (MM/DD/YYYY) 1325 | ENDING EFFECTIVE DATE (MM/DD/YYYY) 1330 | RATE TYPE - PRE-PAID/FFS (P/F) 1335 | PRE-PAID MONTH'S NOTICE 1340 | FFS MONTH'S NOTICE 1345 |
|---|---|---|---|---|---|---|---|---|
| patch_adams | Primary Care Internal Medicine | Physician | 87654321 | 10/01/1999 | 01/01/9999 | P | 1 | 1 |
| little_boo | Dentist | Physician | 86003201 | 10/07/1999 | 01/01/9999 | P | 2 | 1 |
| john_anderson | Gynecology | Physician | 99776655 | 10/15/1999 | 01/01/9999 | P | 4 | 1 |

SPONSOR INFORMATION DATABASE 1400

| LOG-IN IDENTIFIER 1405 | SPONSOR NAME 1410 | ADDRESS 1420 | CONTACT NAME 1425 | CONTACT PHONE # 1430 | E-MAIL ADDRESS 1435 | TYPE OF SPONSOR (E/H/S/O) 1440 | SPONSOR ID CODE 1445 |
|---|---|---|---|---|---|---|---|
| mifune_go | Race Co X Mfg. | 1 Cartoon Way Race City, IN 46224 | Trixie Racer | 3175556224 | speed@racecox.com | E | RACECOX |
| robert_m_blind | Tifosi Life Co. | PO Box 1 Maranello, IL 60666 | Robert M. Blind | 3125555431 | robmblind@tinsurance.com | H | TIFOSILIFECO |
| wizigco | Wizig & Company | 1211 W 17 ST Hometown, KS 66211 | Howard Wizig | 9135552112 | wizig@aol.com | E | WIZIG&CO |

SPONSORED INDIVIDUAL DATABASE 1500

| SPONSOR ID CODE 1505 | SUB-SPONSOR ID 1510 | SPONSOREE ID 1515 | SPONSOREE NAME 1520 | CONTRIBUTION 1525 | INITIAL PASSWORD 1530 |
|---|---|---|---|---|---|
| WIZIG&CO | WIZIG&CO | 3452112 | JOHN MICHAEL JONES | 5000 | JMJ2112 |
| WIZIG&CO | WIZIG&CO | 3452122 | HAYLEY CLAIRE LYNN | 5000 | HCL2112 |
| WIZIG&CO | WIZIG&CO | 3452132 | MARISSA LYNN HOWARD | 5000 | MLH2132 |

CPT DATABASE 1600

| LOG-IN IDENTIFIER 1605 | PROVIDER ID 1610 | CATEGORY 1615 | CPT CODE 1620 | BEGINNING EFFECTIVE DATE (MM/DD/YYYY) 1625 | ENDING EFFECTIVE DATE (MM/DD/YYYY) 1630 |
|---|---|---|---|---|---|
| patch_adams | 87654321 | PRIMARY CARE INTERNAL MEDICINE | 99201 | 10/01/1999 | 01/01/9999 |
| patch_adams | 87654321 | PRIMARY CARE INTERNAL MEDICINE | 99211 | 10/01/1999 | 01/01/9999 |
| patch_adams | 87654321 | PRIMARY CARE INTERNAL MEDICINE | 99212 | 10/01/1999 | 01/01/9999 |

PHYSICIAN BACKGROUND DATABASE 1700

| LOG-IN IDENT-IFIER 1705 | PHYSICIAN NAME 1710 | EDUCATION/ TRAINING 1715 | BOARD CERTS 1720 | OFFICE LOC-ATION 1725 | OFFICE HOURS 1730 | MEDICAL GRP PTRS 1735 | PROVIDER ID 1740 |
|---|---|---|---|---|---|---|---|
| patch_adams | PATCH A. ADAMS, MD | MD - Univ. of Penn., Internal Med. Res. At Duke University | NONE | 2335 Kingshighway St. Louis, MO 63112 | M - TR (8:30a - 3p) | Harold Butcher John Akers | 87654321 |
| cut_up | HAROLD BUTCHER, MD | MD - Univ. of No-where, Surgery Res. At Tulane Univ. | NONE | 2335 Kingshighway St. Louis, MO 63112 | M - TR (8:30a - 3p) | Patch Adams John Akers | 87666333 |
| slow-hand | JOHN AKERS, MD | MD - Univ. of Texas, Surgery Res. At Washington Univ. | NONE | 2335 Kingshighway St. Louis, MO 63112 | M - TR (8:30a - 3p) | Patch Adams Harold Butcher | 994444271 |

RATES DATABASE  1800

| LOG-IN IDENTIFIER 1805 | PROVIDER ID 1810 | CATEGORY 1815 | RATE TYPE - PRE-PAID/FFS (P/F) 1817 | AGE CAT. 1820 | MONTHLY RATE (Male) 1825 | MONTHLY RATE (Female) 1830 | CO-PAYMENT 1835 | BEGINNING EFFECTIVE DATE (MM/DD/YYYY) 1840 | ENDING EFFECTIVE DATE (MM/DD/YYYY) 1845 |
|---|---|---|---|---|---|---|---|---|---|
| patch_adams | 87654321 | Primary Care Internal Medicine | P | 0 - 4 | $ 20 | $ 22 | $ 15 | 10/01/1999 | 01/01/9999 |
| patch_adams | 87654321 | Primary Care Internal Medicine | P | 5 - 9 | $ 23 | $ 27 | $ 15 | 10/01/1999 | 01/01/9999 |
| patch_adams | 87654321 | Primary Care Internal Medicine | P | 40 - 44 | $ 60 | $ 63 | $ 20 | 10/01/1999 | 01/01/9999 |

REFERRAL DATABASE  1900

| LOG-IN IDENTIFIER 1905 | REFERRER PROVIDER ID 1908 | BEGINNING EFFECTIVE DATE (MM/DD/YYYY) 1910 | ENDING EFFECTIVE DATE (MM/DD/YYYY) 1915 | CATEGORY 1920 | PROVIDER NAME 1925 | REFERREE PROVIDER ID 1930 | REFERRAL PANEL ID 1935 |
|---|---|---|---|---|---|---|---|
| patch_adams | 87654321 | 10/01/1999 | 10/01/9999 | Primary Care Internal Medicine | PATCH ADAMS, MD | 87654321 | 321 |
| patch_adams | 87654321 | 10/01/1999 | 10/01/9999 | Cardiology | MARISSA WIZIG, MD | 60771359 | 321 |
| patch_adams | 87654321 | 10/01/1999 | 10/01/9999 | Gynecology | JOHN ANDERSON, MD | 99776655 | 321 |
| patch_adams | 87654321 | 10/01/1999 | 10/01/9999 | Dermatology | JERALD SKLAR, MD | 304659413 | 321 |
| patch_adams | 87654321 | 10/01/1999 | 10/01/9999 | Inpatient Hospital | GENERAL HOSPITAL | 209413994 | 321 |

Are you a:

- Consumer/Purchaser
  Number of Family Members ☐ (including yourself)

- Physician, Hospital, or other Healthcare Provider

- Sponsor (Employer, Insurance Carrier, Etc.)

Select your User ID: _____

Select your Password: _____

Your E-mail Address: _____

Your Home ZIP Code: _____

☐ Check Here if you would like to save this information on your PC ("Cookies")

[PREVIOUS]  [NEXT]

Who is sponsoring your purchase?

○ Self
  Please enter an annual amount that you would like to budget on a healthcare services package $ ☐
  (enter 0 if you are seeking price estimates)

○ Employer

○ Insurer, HMO, or other Healthcare Administrator

PREVIOUS   NEXT

FIG. 22

Please enter the following information:

Employer ID Code: _____

Your Employee ID Code: _____

Your Employee ID Password: _____ (Search)

[PREVIOUS] [NEXT]

FIG. 23

Your Name: JOHN MICHAEL JONES

Your Employer: WIZIG & COMPANY

Total Employer Contribution Available: $5,000.00

PREVIOUS  NEXT

FIG. 24

Select the Person for whom you want to build/modify a healthcare panel (you may select more than one name if they want to share the same panel):

○ JOHN MICHAEL JONES

○ JENNY LEE JONES

○ JULIA LYNN JONES

PREVIOUS   NEXT

FIG. 25

JENNY LEE JONES

How do you want to build your healthcare panel:

- Let me start with a panel built around my chosen Primary Physician
- Let me start with a panel built around my chosen Hospital
- Let me start with the lowest cost
- Let me build a customized panel

PREVIOUS  NEXT

FIG. 26

JENNY LEE JONES

Primary Physician Selection: PATCH A ADAMS, M.D. ▼ SELECT (More Information)

SEARCH:

| Name | ZIP Code | Distance | Value | Price | Hospital Affiliation |
|------|----------|----------|-------|-------|----------------------|
| O | O | O | O | O | O |

SEARCH

FIG. 27

Next to each category you will see a list of the healthcare providers named by your Primary Physician. In some categories, the Primary Physician you selected has named more than one healthcare provider. We will sort these names for you, based on criteria you select below, and the name best matching your criteria will be listed first. You can use the drop down menu next to the category to see the other providers named by your chosen Primary Physician, or you can use your own criteria to search for additional providers (who were not named by your Primary Physician). You can always select "none" if you do not want to pre-purchase services in that category.

Search Criteria:

| | Priority | | | | | |
|---|---|---|---|---|---|---|
| | 1 | 2 | 3 | 4 | 5 | |
| Distance (miles) | O | O | O | O | O | WITHIN 5 MILES ▶ |
| Distance (time) | O | O | O | O | O | WITHIN 15 MINUTES ▶ |
| Value | O | O | O | O | O | TOP 5% ▶ |
| Price | O | O | O | O | O | LOWEST PRICE ▶ |
| Hospital Affiliation | O | O | O | O | O | GENERAL HOSPITAL ▶ |

If your selected Primary Physician did not name a provider in a category do you want us to use the same criteria to that you selected above to identify a provider for you?      O Yes      O No

PREVIOUS    NEXT

FIG. 28

Select your default Co-payment that will be loaded, for your convenience, in each category. You may always use the drop-down menu on the next page to select a different co-payment in any healthcare category.

$15 ▶

If the default co-payment that you selected above is not available in one (or more) of the healthcare categories, would you like us to choose the closest available co-payment? You will always be able to use the drop down menu on the next page to select a different co-payment in any healthcare category.

○ Yes, (Break a tie by going to the next lower co-payment)
○ Yes, (Break a tie by going to the next higher co-payment)
○ No, leave it blank and I will select the co-payment

PREVIOUS    NEXT

FIG. 29

JENNY LEE JONES

| | | | | Co-payment |
|---|---|---|---|---|
| PRIMARY CARE PHYSICIAN: | PATCH A. ADAMS, M.D. ▼ | (Search) | (More Info) | $ 20.00 ▼ |
| INPATIENT HOSPITAL: | GENERAL HOSPITAL ▼ | (Search) | (More Info) | $ 500.00 ▼ |
| OBSTETRICIAN: | NONE ▼ | (Search) | (More Info) | NOT APPL. ▼ |
| GYNECOLOGIST: (excludes Obstetrics) | JOHN ANDERSON, M.D. ▼ | (Search) | (More Info) | $ 20.00 ▼ |
| CARDIOLOGIST: | MARISSA WIZIG, M.D. ▼ | (Search) | (More Info) | $ 20.00 ▼ |
| DERMOTOLOGIST: | JERALD SKLAR, M.D. ▼ | (Search) | (More Info) | $ 20.00 ▼ |
| UROLOGIST: | NEAL MATTHIEW, D.O. ▼ | (Search) | (More Info) | $ 20.00 ▼ |
| EMERGENCY ROOM: | ST. ANYWHERE E.R. ▼ | (Search) | (More Info) | $ 20.00 ▼ |
| PHARMACY: | DIANE'S DRUGS ▼ | (Search) | (More Info) | $ 20.00 ▼ |
| DENTAL: | HAYLEY WIZIG, D.D.S. ▼ | (Search) | (More Info) | $ 20.00 ▼ |
| VISION: | BETH OLIAK, M.D. ▼ | (Search) | (More Info) | $ 20.00 ▼ |
| UMBRELLA POLICY: | TIFOSI LIFECO ▼ | (Search) | (More Info) | $ 2,000.00 ▼ |

TOTAL BUDGET REMAINING
$ 2,975.00

THIS PANEL'S SUB-TOTAL
$ 2,025.00

INCREASE (DECREASE) DUE TO LAST MODIFICATION
($ 123.99)

[PREVIOUS] [NEXT]

FIG. 30

JENNY LEE JONES

Below is the list of physicians, hospitals, and other healthcare providers that have been selected:

| | | | |
|---|---|---|---|
| PRIMARY CARE PHYSICIAN: | PATCH A. ADAMS, M.D. ▼ | (Search) (More Info) | $ 20.00 ▼ |
| INPATIENT HOSPITAL: | GENERAL HOSPITAL ▼ | (Search) (More Info) | $ 500.00 ▼ |
| OBSTETRICIAN: | NONE ▼ | (Search) (More Info) | NOT APPL. ▼ |
| GYNECOLOGIST: (excludes Obstetrics) | JOHN ANDERSON, M.D. ▼ | (Search) (More Info) | $ 20.00 ▼ |
| CARDIOLOGIST: | MARISSA WIZIG, M.D. ▼ | (Search) (More Info) | $ 20.00 ▼ |
| DERMOTOLOGIST: | JERALD SKLAR, M.D. ▼ | (Search) (More Info) | $ 20.00 ▼ |
| UROLOGIST: | NEAL MATTHIEW, D.O. ▼ | (Search) (More Info) | $ 20.00 ▼ |
| EMERGENCY ROOM: | ST. ANYWHERE E.R. ▼ | (Search) (More Info) | $ 20.00 ▼ |
| PHARMACY: | DIANE'S DRUGS ▼ | (Search) (More Info) | $ 20.00 ▼ |
| DENTAL: | HAYLEY WIZIG, D.D.S. ▼ | (Search) (More Info) | $ 20.00 ▼ |
| VISION: | BETH OLIAK, M.D. ▼ | (Search) (More Info) | $ 20.00 ▼ |
| UMBRELLA POLICY: | TIFOSI LIFECO ▼ | | $ 2,000.00 ▼ |

| EDIT | SAVE WITHOUT CHECKING OUT | BUILD THE PANEL FOR ANOTHER FAMILY MEMBER | CHECKOUT |

FIG. 31

|  | Monthly | Annual |
|---|---|---|
| Total Budget | $ 416.67 | $ 5,000.00 |
| Total Price of Each Panel: | | |
| JOHN MICHAEL JONES | $ 195.65 | $ 2,347.80 |
| JENNY LEE JONES | $ 168.75 | $ 2,025.00 |
| JULIA LYNN JONES | $ 47.02 | $ 564.24 |
| Total | $ 411.42 | $ 4,937.04 |
| Balance | $ 5.25 | $ 62.96 |

CHECKOUT    EDIT

FIG. 32

YOUR PURCHASE HAS BEEN COMPLETED
*Please print this page*

Below is the list of physicians, hospitals, and other healthcare providers that have been selected:

JENNY LEE JONES

| | | Co-payment |
|---|---|---|
| PRIMARY CARE PHYSICIAN: | PATCH A. ADAMS, M.D. | $ 20.00 |
| INPATIENT HOSPITAL: | GENERAL HOSPITAL | $ 500.00 |
| OBSTETRICIAN: | NONE | NOT APPLICABLE |
| GYNECOLOGIST (excludes Obstetrics): | JOHN ANDERSON, M.D. | $ 20.00 |
| CARDIOLOGIST: | MARISSA WIZIG, M.D. | $ 20.00 |
| DERMOTOLOGIST: | JERALD SKLAR, M.D. | $ 20.00 |
| UROLOGIST: | NEAL MATHIEW, M.D. | $ 20.00 |
| EMERGENCY ROOM: | ST. ANYWHERE E.R. | $ 20.00 |
| PHARMACY: | DIANE'S DRUGS | $ 20.00 |
| DENTAL: | HAYLEY WIZIG, D.D.S. | $ 20.00 |
| VISION: | BETH OLIAK, M.D. | $ 20.00 |
| UMBRELLA POLICY: | TIFOSI LIFECO | $2,000.00 |

[PRINT] [HOME]

FIG. 33

Please select one of the following options:

○ Profile Information - Create or Update profile information

○ Identify Services Offered

○ Review, Load or Update your Rates

○ Load or Update your Referral List

○ Reports

[PREVIOUS] [NEXT]

FIG. 34

Please identify the Primary type of service that you provide:

○ Physician
○ Dentist
○ Physical Therapist
○ Social Worker
○ Speech and/or Language Therapist
○ Other Medical Practitioner
○ Inpatient Hospital
○ Pharmacy
○ Laboratory
○ Diagnostic Imaging Center
○ Urgent Care Facility
○ Home Health or Home Infusion Provider
○ Durable Medical Equipment Provider
○ Other

PREVIOUS    NEXT

FIG. 35

Enter the following information:

Educational and Training Background (Undergraduate, Medical School, Fellowship, Residency, etc)

Board Certifications

Office Locations and Hours

Medical Group Partners

UPIN Number

PREVIOUS   NEXT

FIG. 36

Identify Service Category(s):

- CARDIOVASCULAR AND THORACIC SURGERY
- PRIMARY CARE: INTERNAL MEDICINE
- ADD A NEW CATEGORY
- DELETE A CATEGORY

[PREVIOUS] [NEXT]

FIG. 37

Select the new service category in which you would like to offer Physician Services:

- Allergy and Immunology
- Anesthesiology
- Cardiovascular and Thoracic Surgery
- Cardiovascular Disease
- Chiropractic
- Colon and Rectal Surgery
- Critical Care
- Dermatology
- Diagnostic Radiology
- Emergency Medicine
- Endocrinology
- Gastroenterology
- Gynecology
- Gynecologic Oncology
- Hand Surgery
- Hematology and Oncology
- Infectious Disease
- Primary Care: Family Practice
- Primary Care: General Practice
- Primary Care: Geriatrics
- Primary Care: Internal Medicine
- Primary Care: Pediatrics
- Maternal and Fetal Medicine
- Medical Oncology
- Neonatology
- Nephrology
- Neurological Surgery
- Nerurology
- Neuclear Medicine
- Obstetrics
- Opthamology
- Oral and Maxilofacial Surgery
- Orthopedic Surgery
- Otolaryngology (ENT)
- Pathology
- Pediatric Surgery
- Physical Medicine and Rehabilitation
- Plastic and Reconstructive Surgery
- Podiatry
- Psychiatry
- Psycologist
- Pulmonary Disease
- Rheumatology
- Sports Medicine
- Therapeutic Radiology
- Transplant Surgery
- Urology
- Vascular Surgery Beginning effective date of the new service category [ / / ]

[PREVIOUS] [NEXT]

FIG. 38

Select the new service category in which you would like to offer Non-Physician Services:

○ Inpatient Hospital
○ Emergency Room & Urgent Care
○ Pharmacy
○ Radiology Centers
○ Lab
○ Home Infusion Therapy
○ Durable Medical Equipment
○ Physical Therapy
○ Social Worker
○ Speech and Language Pathology
○ Dentist Beginning effective date of the new service category [ / / ]

[PREVIOUS]  [NEXT]

FIG. 39

The purpose of this Page is to identify the services included in your rates (by CPT Code). You must provide all of the services that you include in your rates:

- ○ Review standardized list(s) of CPT Codes that are typically included in this service category

- ○ Add a standardized list of CPT Codes that are typically included in this service category
  (note that you may delete some of these services and/or add additional services before finalizing your list of services)

- ○ Add individual CPT Codes (or Ranges of CPT Codes)

- ○ Delete individual CPT Codes (or Ranges of CPT Codes)

- ○ Review your current list CPT Codes for this service category (includes all modifications made to date)

- ○ Effective Date of Changes
  (note that changes for individual consumers that have already selected you for this service category will not become effective until the consumers next renewal date)

- ○ Finalize your list of CPT Codes for this service category

[PREVIOUS] [NEXT]

FIG. 40

Identify the Service Category:   O CARDIOVASCULAR AND THORACIC SURGERY
                                 O PRIMARY CARE: INTERNAL MEDICINE Identify the Type of Rates:   O Pre-Paid
                              O Fee-For-Service

PREVIOUS    NEXT

FIG. 41

Please select one of the following options:

Review Your Current Rates

Modify or Load Rates

Modify Required Notice of Changes from Patients

PREVIOUS    NEXT

FIG. 42

Select one of the following rate options:

O Enter new rates, or modify individual rates

O Apply a single Percentage adjustment to rates (Example: add 2.00%)
   Note: You may select all co-payments, or individual co-payment(s)

O Apply a dollar adjustment to rates (example: Add $0.01 PMPM)
   Note: You may select all co-payments, or individual co-payment(s)

[PREVIOUS] [NEXT]

FIG. 43

Please select one of the following options:

O  Manually Enter Rates for each Co-payment and Age/Gender Category

O  Create a set of Percentage Adjustment Tables that will develop all rates by applying a percentage adjustment to your chosen "standard" age/gender category
(example: if you set a 40-44 year old male as your "standard", then you could set the 40-44 year old female to be 105% of the 40-45 year old male rate)

O  Tools
(Various Adjustment Tables that you may want to consider when building your Rate Tables; including free tables from BuyMedDirect.Com that reflect the straight average, weighted average, and median ratio within the service category or across categories, and including tables which can be purchased from Actuarial firms)

PREVIOUS    NEXT

FIG. 44

Select the Co-payment: ○ $ 5   ○ $20   ○ $35
○ $10  ○ $25   ○ Other
○ $15  ○ $30

Enter the Monthly Rate for Pre-paid Services per Consumer (enter a 0 if you do not offer the service to an Age/Gender category):

| Age: | Male | Female |
|---|---|---|
| 0-4 | $ | $ |
| 5-9 | $ | $ |
| 10-14 | $ | $ |
| 15-19 | $ | $ |
| 20-24 | $ | $ |
| 25-29 | $ | $ |
| 30-34 | $ | $ |
| 35-39 | $ | $ |
| 40-44 | $ | $ |
| 45-49 | $ | $ |
| 50-54 | $ | $ |
| 55-59 | $ | $ |
| 60-64 | $ | $ |
| 65-69 | $ | $ |
| 70-74 | $ | $ |
| 75-80 | $ | $ |
| 80-84 | $ | $ |
| 85-89 | $ | $ |
| 90 and over | $ | $ |

[PREVIOUS]   [SUBMIT THESE RATES - NEXT]

FIG. 45

Note that all Consumers/Patients are allowed to select services at the time of Open Enrollment. However, some patients choose to change their selection within their medical plan year. Due to potential "anti-selection" concerns of some physicians, you are allowed to determine how much advance notice you require to accept a new pre-paid patient. Please recognize, however, that more restrictive your notice period, the less attractive you may be to these potential patients. As long as you continue to participate with BuyMedDirect.Com, you agree to accept new patients who provide at least 4 months notice (as defined below)

Patients with Pre-Paid Care:

How much notice do you require for patients who currently have a pre-paid physician in this category, but want you to be their chosen physician

- ○ No Advance Notice Required
- ○ 1 Month Notice (Change effective on the 1st day of the next Calendar Month)
- ○ 2 Month Notice (Change effective on the 1st day of the month after the next Calendar Month)
- ○ 3 Month Notice (Change effective on the 1st day of the month that is two months after the next Calendar Month)
- ○ 4 Month Notice (Change effective on the 1st day of the month that is three months after the next Calendar Month)

Patients without Pre-Paid Care:

How much notice do you require for patients who currently do not have a pre-paid physician in this category

- ○ No Advance Notice Required
- ○ 1 Month Notice (Change effective on the 1st day of the next Calendar Month)
- ○ 2 Month Notice (Change effective on the 1st day of the month after the next Calendar Month)
- ○ 3 Month Notice (Change effective on the 1st day of the month that is two months after the next Calendar Month)
- ○ 4 Month Notice (Change effective on the 1st day of the month that is three months after the next Calendar Month)

[ PREVIOUS ]  [ NEXT ]

FIG. 46

The purpose of this Page is to identify the list of physicians, hospitals, and other healthcare providers with whom you refer services. This list will be used by Consumers who seek to build their healthcare panel around your selections:

O Review standardized panel(s) such as a PHO, IPA, or the panel developed by one of your peers.

O Add a standardized referral panel
(note that you may delete or add to this list before finalizing your personalized referral panel)

O Add individual physicians, hospitals, or other healthcare providers

O Delete individual physicians, hospitals, or other healthcare providers

O Review your personalized referral panel (includes all modifications made to date)

O Finalize your personalized referral panel

PREVIOUS    NEXT

FIG. 47

Please select one of the following options:

O Confirm status of an Individual Patient

List Pre-Paid Consumers/Patients:

O All Current Consumers/Patients
    O New Consumers/patients
    O Terminated Consumers/Patients
    O Consumers/Patients in a Prior Month O Report Rates Summary Report of:

O Monthly Rate Information by Age/Gender/Co-payment
    O Monthly Rate Information by Age/Gender
    O Monthly Rate Information by Co-payment
    O Prepaid Consumers by Age/Gender/Co-payment
    O Prepaid Consumers by Age/Gender
    O Prepaid Consumers by Co-payment

[PREVIOUS] [NEXT]

FIG. 48

Please select one of the following options:

○ Profile Information - Create or Update profile information

○ Generate Reports

○ Add, Review or Edit Sponsored Plan Members and Contributions

○ Add a New Plan Member; Number to be added: ☐
○ Review Plan Members
○ Edit Plan Members

PREVIOUS    NEXT

FIG. 49

Enter the following information:

Sponsor Name

Sponsor Address

Contact Name

Contact Phone Number

Type of Sponsor:
○ Insurer
○ Employer
○ Other

Sponsor ID Code

[PREVIOUS] [NEXT]

FIG. 50

Please review the following list of sponsored plan members:

| Name of Plan Member | Sponsor Contribution | Sub-Sponsor or Employer ID Code | Sponsoree ID Code | Initial Sponsoree ID Password |
|---|---|---|---|---|
| JOHN MICHAEL JONES | $ 5,000.00 | Wizig&Company | 3452112 | abdfgi97 |
| HAYLEY CLAIRE LYNN | $ 5,000.00 | Wizig&Company | 3452122 | bcdfgi97 |
| MARISSA LYNN HOWARD | $ 5,000.00 | Wizig&Company | 3452132 | dhdfgi97 |

PREVIOUS  NEXT

FIG. 51

Please use the form below to add sponsored plan members:

| Name of Plan Member | Sponsor Contribution | Sub-Sponsor or Employer ID Code | Sponsoree ID Code | Initial Sponsoree ID Password |
|---|---|---|---|---|
| | $ | | | |
| | $ | | | |
| | $ | | | |
| | $ | | | |

PREVIOUS  NEXT

FIG. 52

Please edit the following list of sponsored plan members:

| Name of Plan Member | Sponsor Contribution | Sub-Sponsor or Employer ID Code | Sponsoree ID Code | Initial Sponsoree ID Password |
|---|---|---|---|---|
| JOHN MICHAEL JONES | $ 5,000.00 | Wizig&Company | 3452112 | abdfgi97 |
| HAYLEY CLAIRE LYNN | $ 5,000.00 | Wizig&Company | 3452122 | bcdfgi97 |
| MARISSA LYNN HOWARD | $ 5,000.00 | Wizig&Company | 3452132 | dhdfgi97 |

PREVIOUS  NEXT

FIG. 53

Please select one of the following options:

Report Plan Members and Dependents:
○ By Geographic Area
○ Employer or Business Unit
○ By Annual Effective Date
○ By Contribution Amount Report Contribution Amount and Healthcare Service Package Costs:
○ Aggregate Information by Month
○ Aggregate Information by Employer or Business Unit
○ Aggregate Information by Annual Effective Date
○ Aggregate Information by Geographic Area
○ Detailed Information by Month
○ Detailed Information by Employer or Business Unit
○ Detailed Information by Annual Effective Date
○ Detailed Information by Geographic Area

|PREVIOUS| |NEXT|

FIG. 54

Express Buy

Click on the Express Buy button above to purchase a complete panel of healthcare providers based on the Search Criteria you chose on the prior page.

Custom Buy

Identify the services that you want to Express Buy, Custom Buy or Exclude

Category 1
Services are often Custom Buy or usually exceed 2% of the cost

| Express Buy | Custom Buy | Exclude | |
|---|---|---|---|
| O | O | O | Primary Care Physician |
| O | O | O | Inpatient Hospital |
| O | O | O | Obstetrician |
| O | O | O | Gynecologist |
| O | O | O | Dermatologist |
| O | O | O | Urologist |
| O | O | O | Emergency Room |
| O | O | O | Pharmacy |
| O | O | O | Dental |
| O | O | O | Vision |
| O | O | O | Umbrella Policy |

Category 2
Services are occasionally Custom Buy. (List of Category 2 Services)

○ Express Buy Category 2 Services
○ Custom Buy Category 2 Services
○ Exclude Category 2 Services

Category 3
Services are infrequently Custom Buy. (List of Category 3 Services)

○ Express Buy Category 3 Services
○ Custom Buy Category 3 Services
○ Exclude Category 3 Services

FIG. 55

METHOD AND SYSTEM FOR PROVIDING A USER-SELECTED HEALTHCARE SERVICES PACKAGE AND HEALTHCARE SERVICES PANEL CUSTOMIZED BASED ON A USER'S SELECTIONS

RELATED APPLICATIONS AND PRIORITY CLAIM

This is a Continuation of prior application Ser. No. 09/434,271, filed Nov. 4, 1999, now U.S. Pat. No. 6,735,569, entitled, "Method and system for providing a user-selected healthcare services package and healthcare services panel customized based on user's selections," to which priority under 35 U.S.C. §120 is claimed. The entire contents of the aforementioned application are herein expressly incorporated by reference.

FIELD OF THE INVENTION

This invention relates generally to a system and method for online selection of healthcare services and, more particularly, to a system and method for allowing a user to select a customized healthcare services panel and for providing the user with a healthcare services package, the cost of which is calculated based on the users selections.

BACKGROUND OF THE INVENTION

The majority of healthcare in the United States is sponsored by employers, because, unlike most of its European counterparts, the United States does not automatically provide healthcare services on a no-cost basis to all of its citizens. Generally, an employer selects and contracts with a third party administrator to administer its health benefits program funded either by the employer buying insurance or by self-funding the program (self-insurance).

Historically, employers sponsored "Traditional Indemnity" programs where employees and their dependents were free to choose and utilize the services of any healthcare service provider and be reimbursed for covered benefits, less some form of cost sharing such as an annual deductible or co-insurance. For example, a covered employee was responsible for the first $100 in annual covered benefits ("deductible"), for 20% of the next $5,000 (i.e., a $1,000 annual co-insurance limit), and was fully reimbursed for the amount that the years claims exceed $5,000. Because the employee was paying only a minority of the cost of healthcare services, the employee was not sensitive to the cost and healthcare service providers rarely competed on the basis of price. However, healthcare service providers did compete based on other attributes such as technology, and the advent of expensive new technologies further drove costs upward and resulted in the cost of employers' healthcare programs spiraling sharply upward in the 1980s and early 1990s.

In response to the rapidly rising costs of their healthcare programs, employers have increasingly turned to Managed Care Organizations ("MCOs") such as Health Maintenance Organizations ("HMOs") and Preferred Provider Organizations ("PPOs"). MCOs develop restricted networks of healthcare service providers who are willing to accept a negotiated level of reimbursement which is typically much lower than the provider's standard fees. Because the employer (and not the employee/dependent) is the customer of the MCO, the employee/dependent has virtually no voice in the selection of the MCO's provider network. Employees who go outside the MCO's provider network typically receive no benefits from traditional HMOs and typically receive dramatically reduced benefits from PPOs or "Point of Service" HMO programs.

MCOs have also implemented extensive programs designed to further manage the cost of healthcare. Most of these Utilization Management ("UM") programs are designed to reduce utilization and restrict the delivery of care. Examples of UM programs include precertification programs which require prior authorization from the MCO before a physician can refer a patient to another physician, order a procedure or test or admit a patient to a hospital. Some MCO programs require that a Primary Care Physician ("PCP") be selected by each covered member, and that the PCP must act as a "gatekeeper" to authorize referrals to other physicians.

MCOs also rely heavily on the collection of utilization and claim information in order to administer their programs and to manage the risk associated with healthcare costs. MCOs utilize a variety of methodologies to manage the risk, including both risk sharing and risk transfer to healthcare service providers. Some of the MCO risk sharing and risk transfer methodologies have become quite controversial and have therefore become subject to increased scrutiny, e.g., placing a physician at risk for the cost of his referrals of patients to specialists or hospitals.

In light of the above, it is not surprising that MCO's chosen by and designed for employers are generally ill-favored by both employees and healthcare service providers. Unfortunately, the reality is that healthcare coverage is a business-to-business product in the United States, and not a consumer product. Employee dissatisfaction generally stems from the following shortcomings of the MCO programs: (1) the limited provider network may not include their desired physician or hospital; (2) the administrative and utilization management requirements of the program are often burdensome and frustrating; and (3) the benefit design chosen by the employer often does not meet the particular needs of the employee.

Physicians, hospitals and other healthcare service providers are generally discontent with MCOs because: (1) the administrative costs and paperwork are unduly burdensome; (2) the UM programs imposed by MCOs are both administratively cumbersome and expensive; and (3) the provider contracts offered by MCOs allows the MCO to unilaterally dictate the price, terms, and administrative requirements; and (4) the profits and administrative fees charged by MCOs is believed to be at the expense of patient care.

Ideally, healthcare service providers should be able to contract more directly with patients and employers, thereby reducing the role of intermediaries such as MCOs. Furthermore, employees and their families should be able to be "consumers" and make their healthcare purchasing decisions. Finally, employers should be afforded relief from both unpredictable and rising increases in their costs of sponsoring healthcare programs for their employees.

Accordingly, a need exists for a healthcare coverage system and method that allows individuals to contract for the healthcare services that they need, from the healthcare providers that they prefer, and at a price that is within their financial restraints. In other words, to empower the individual as a consumer. There further exists a need to implement Web sites on the Internet to reduce the administration costs of implementing such a healthcare coverage system and to facilitate the registration of individual members into the system. Finally, there exists the need to provide a mechanism that allows healthcare service providers to offer their services to consumers who seek to build a customized healthcare services package, while providing the healthcare service providers stable and predictable fixed monthly incomes and manageable patient lists.

SUMMARY OF THE INVENTION

In connection with the foregoing, a method and system is disclosed for allowing a user to select healthcare services where a server generally receives personal information data comprising a user identifier and a financial parameter from the user, provides a list comprising a plurality of healthcare service providers to the user, receives a selection of a healthcare services panel from the user comprising at least one of the healthcare service providers, determines a healthcare services package based on the users selection and the financial parameter and provides the determined healthcare services package to the user for selection of the healthcare services package.

According to one aspect of the invention, the personal information data further comprises a sponsor identifier that identifies the party responsible for paying for all or a portion of the user's healthcare benefits, such as an employer of the user, a healthcare administration company ("HAC") associated with the user (e.g., an insurance company, HMO, or Third Party Administrator), or the user himself.

According to another aspect of the invention, the financial parameter comprises an amount of healthcare benefits available from the employer or the HAC, or an amount of healthcare costs identified by the user.

According to another aspect of the invention, the financial parameter represents that the user is soliciting price estimates.

According to another aspect of the invention, the server receives a selection of an anchor provider by the user, and wherein the list is provided to the user based on the anchor provider.

According to another aspect of the invention, the list is provided to the user based on a predefined criteria or a predefined criteria associated with the anchor provider.

According to another aspect of the invention, the predefined criteria comprises one of the group consisting of: price, quality, ratings, ranking, location, time, distance and hospital affiliation.

According to yet another aspect of the invention, the personal information data further comprises an identification of a plurality of individuals to be associated with the healthcare services package.

According to yet another aspect of the invention, a healthcare services panel is selected by the user for each of the plurality of individuals, and wherein the healthcare services package is further determined based on the healthcare services panels.

According to yet another aspect of the invention, each healthcare service provider is associated with an individual cost ("IC") and an umbrella policy credit ("UPC") and the personal information data further comprises an uncredited umbrella policy cost, and wherein the determination of the healthcare services package comprises aggregating the ICs and UPCs of the healthcare service providers on the healthcare services panel, calculating the difference between the uncredited umbrella policy cost and the aggregated amount of the UPCs, wherein the difference represents a credited umbrella policy cost, and determining the healthcare services package based on the sum of the aggregated ICs and the credited umbrella policy.

According to yet another aspect of the invention, the ICs and UPCs of each healthcare service provider of the healthcare services panels of each of a plurality of individuals are aggregated, the difference between the uncredited umbrella policy cost and the aggregated amount of the UPCs of each of a plurality of individuals is calculated, wherein the difference represents a credited umbrella policy cost, and the healthcare services package is determined based on the sum of the aggregated ICs and the credited umbrella policy cost.

According to yet another aspect of the invention, the determination of the healthcare services package is further based on an amount of deductible on an umbrella policy included in the personal information data.

According to yet another aspect of the invention, an amount of deductible on an umbrella policy is included in the personal information data for each individual.

According to yet another aspect of the invention, the server generally receives from the healthcare service provider information data comprising a provider identifier and a rate parameter, provides the information data to a plurality of users for selection by the users, provides a list to the healthcare service provider comprising the plurality of users that selected the healthcare provider, and provides payment to the healthcare service provider based on the rate parameter.

According to yet another aspect of the invention, the information data further comprises a location and a hospital affiliation of the healthcare service provider, an identification of services included in the rate parameter and/or a referral panel.

According to yet another aspect of the invention, the rate parameter comprises a fixed rate and at least one amount of co-payment.

The system and method of the invention will be more readily understood and apparent from the following detailed description of the invention when read in conjunction with the accompanying drawings, and from the claims which are appended at the end of the detailed description.

BRIEF DESCRIPTION OF DRAWINGS

FIGS. 6A-6B are flow diagrams illustrating an embodiment of a healthcare service provider referrals process.

FIGS. 8A-8C are flow diagrams illustrating an embodiment of a sponsor registration process.

FIG. 9 is a block diagram of the member panel database of FIG. 2.

FIG. 10 is a block diagram of the registration database of FIG. 2.

FIG. 11 is a block diagram of the sponsoree database of FIG. 2.

FIG. 12 is a block diagram of the member demographics database of FIG. 2.

FIG. 13 is a block diagram of the healthcare service provider database of FIG. 2.

FIG. 14 is a block diagram of the sponsor information database of FIG. 2.

FIG. 15 is a block diagram of the sponsored individual database of FIG. 2.

FIG. 16 is a block diagram of the CPT database of FIG. 2.

FIG. 17 is a block diagram of the physician background database of FIG. 2.

FIG. 18 is a block diagram of the rates database of FIG. 2.

FIG. 19 is a block diagram of the referral database of FIG. 2.

FIG. 20 is a diagram illustrating a registration form.

FIG. 21 is a diagram illustrating a demographics request form.

FIG. 22 is a diagram illustrating a sponsorship request form.

FIG. 23 is a diagram illustrating an employer identification request form.

FIG. 24 is a diagram illustrating an employer confirmation page.

FIG. 25 is a diagram illustrating an individual selection page.

FIG. 26 is a diagram illustrating a panel building selection form.

FIG. 27 is a diagram illustrating a Primary Physician identification page.

FIG. 28 is a diagram illustrating a search criteria page.

FIG. 29 is a diagram illustrating a default co-payment form.

FIG. 30 is a diagram illustrating a comprehensive selection registration form.

FIG. 31 is a diagram illustrating a confirmation page.

FIG. 32 is a diagram illustrating a checkout form.

FIG. 33 is a diagram illustrating a purchase confirmation page.

FIG. 34 is a diagram illustrating a healthcare service provider options form.

FIG. 35 is a diagram illustrating an identification of primary services form.

FIG. 36 is a diagram illustrating a background request form.

FIG. 37 is a diagram illustrating an identification of healthcare service categories form.

FIG. 38 is a diagram illustrating a list of physician services form.

FIG. 39 is a diagram illustrating a list of non-physician services form.

FIG. 40 is a diagram illustrating a CPT code form.

FIG. 41 is a diagram illustrating an identification of healthcare service provider rates form.

FIG. 42 is a diagram illustrating a pre-paid options form.

FIG. 43 is a diagram illustrating a rates selection form.

FIG. 44 is a diagram illustrating a rates entry form.

FIG. 45 is a diagram illustrating a rates determination form.

FIG. 46 is a diagram illustrating a notice requirement form.

FIG. 47 is a diagram illustrating a referrals form.

FIG. 48 is a diagram illustrating a reports selection form.

FIG. 49 is a diagram illustrating a sponsor option request form.

FIG. 50 is a diagram illustrating a sponsor profile form.

FIG. 51 is a diagram illustrating a sponsored members form.

FIG. 52 is a diagram illustrating a new member form.

FIG. 53 is a diagram illustrating a user information edit form.

FIG. 54 is a diagram illustrating a sponsor report selection form.

FIG. 55 is a diagram illustrating an express buy form.

DETAILED DESCRIPTION OF INVENTION

Overview of System

Figure 1:
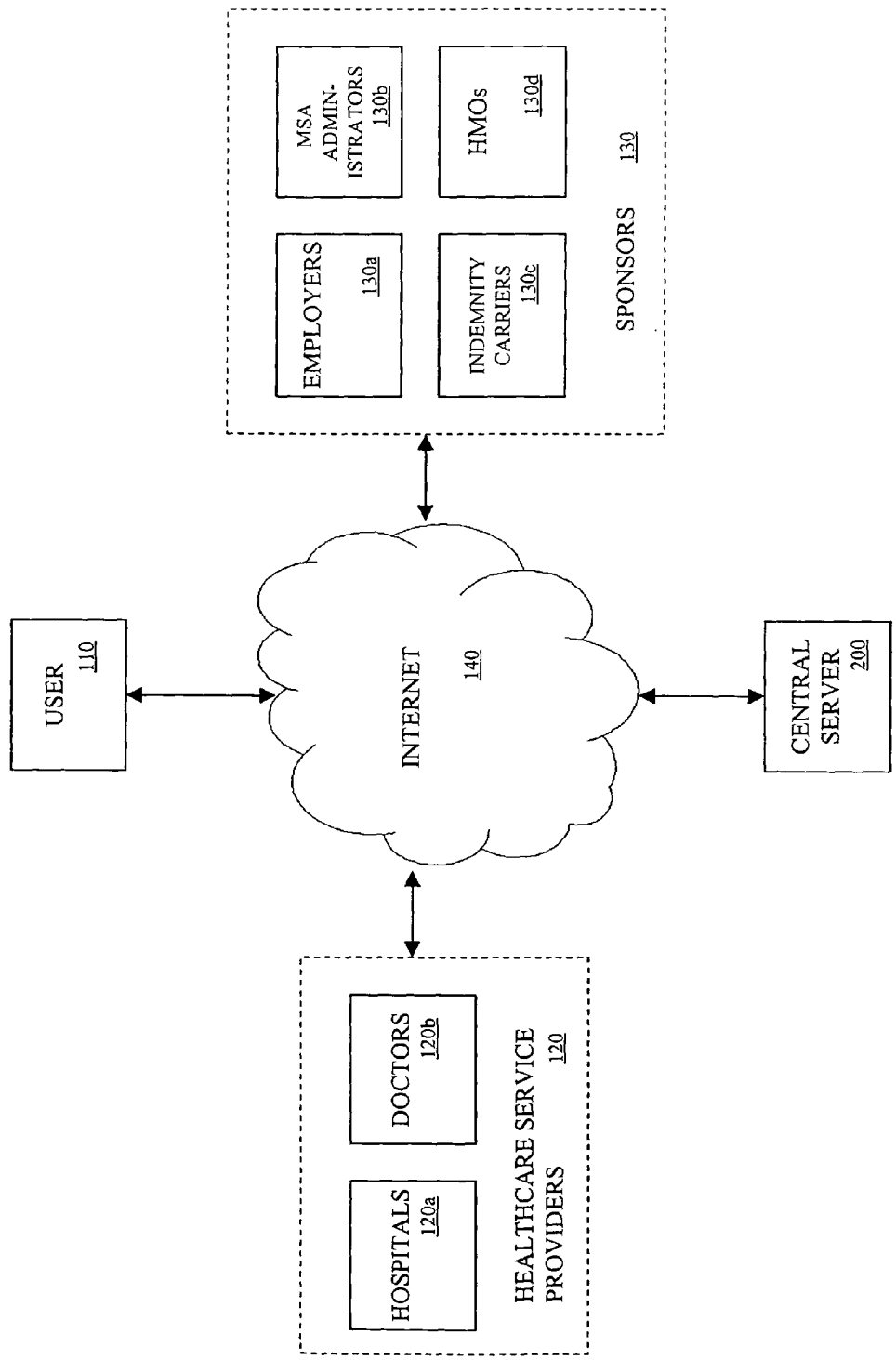
FIG. 1 is a block diagram of a system in accordance with one embodiment of the invention.

FIG. 1 shows a preferred embodiment of a system in accordance with the present invention, where a central server 200 exchanges information over the Internet 140 with a user 110, a plurality of healthcare service providers 120 and a plurality of sponsors 130. Generally, the configuration allows the central server 200 to aggregate information about participating healthcare service providers and sponsored healthcare benefit plans, and to provide the information to the user 110 for selecting and customizing a healthcare services package.

The user 110, healthcare service providers 120 and sponsors 130 (collectively "customers") communicate with the central server 200 by accessing a Web site associated with the central server 200 over the Internet 140 using a Web-browser on their personal computers via an Internet Service Provider ("ISP"; not shown) or by using well-known alternatives to a Web-browser, such as via Web-TV, Palm Pilots, pagers and other personal digital assistants ("PDA's"). The operation of the Internet 140 and access thereto is well-known and is accordingly not described here in detail.

The group of healthcare service providers 120 that communicate with the central server 200, for purposes of illustration, are shown to include hospitals 120a and doctors 120b. As will be discussed in more detail below, the healthcare service providers 120 register with and provide the central server 200 with price, demographical, specialization and affiliation information. The registered healthcare service providers 120 thereafter become available for selection by the user 110, and, if selected, are paid accordingly for their services subject to any co-payment required of the user 110.

The group of sponsors 130 exchanging information with the central server 200, for purposes of illustration, are shown to include employers 130a, medical savings account ("MSA") administrators 130b, indemnity carriers 130c and HMOs 130d. As will be discussed in more detail below, the group of sponsors 130 register with and provide financial information regarding the amount of healthcare benefits available to their plan members. If the user 110 is a plan member, this financial information is accessed and used in the process of determining the user's healthcare services package.

Because of the numerous different types of healthcare service providers 120 and sponsors 130 that may exist, as used in specification and claims, the term "healthcare service provider" and the like shall be understood to include any provider (entity or individual) of a healthcare-related service, for example, entities such as hospitals, laboratories or pharmacies, and individuals such as physicians, physical therapists, social workers or dentists. The term "sponsor" and the like shall be understood to include any individual or entity that finances, administers, or contributes financially to the cost of the user's healthcare package, and in the case where the user 110 is the sole contributor to the cost of his healthcare services package, the sponsor is the user 110 himself. Accordingly, these terms are not limited to the examples listed above.

Central Server

Figure 2:
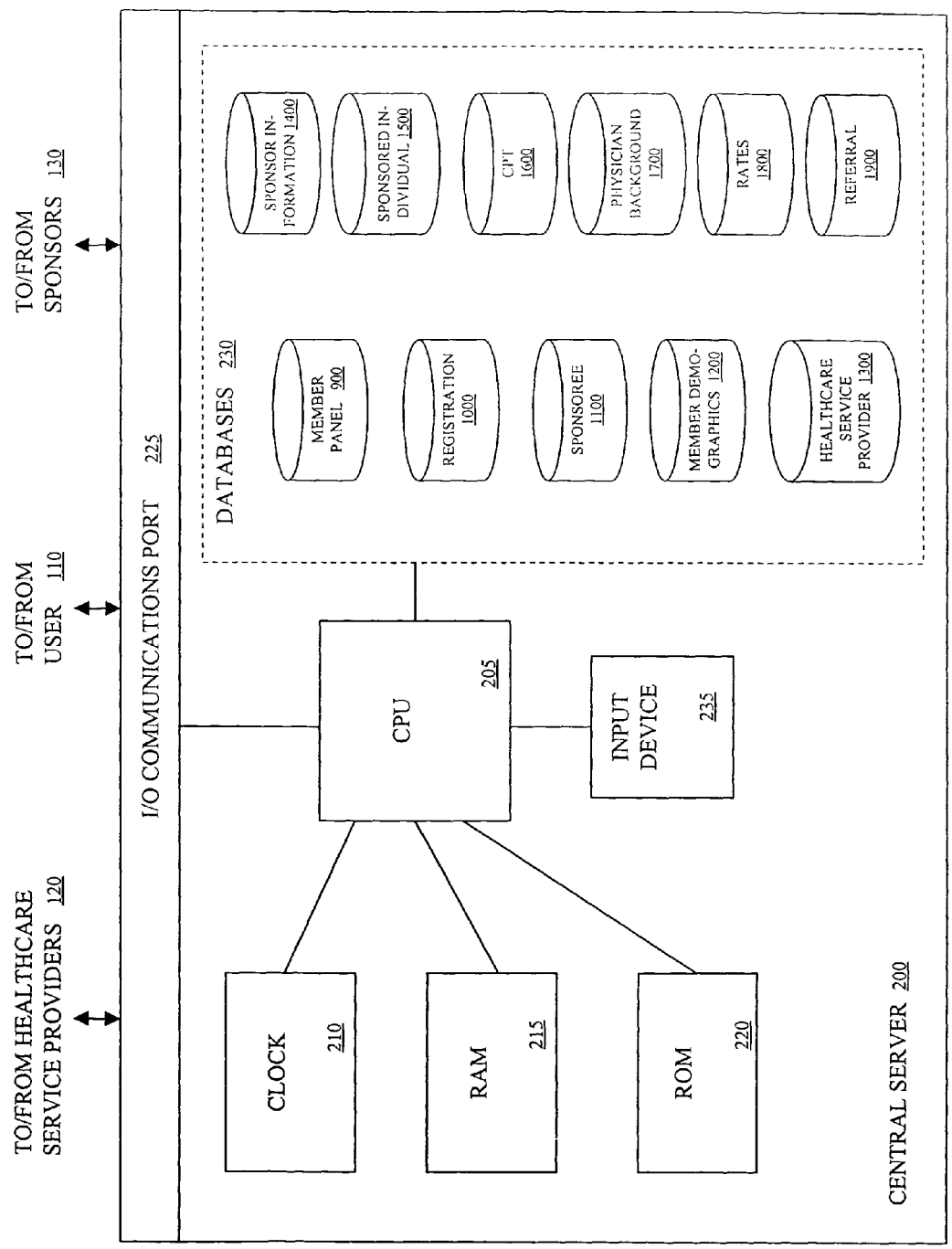
FIG. 2 is a block diagram of the central server of FIG. 1.

FIG. 2 is a block diagram showing the architecture of a preferred embodiment of the central server 200. As FIG. 2 illustrates, the central server 200 includes certain standard hardware components, such as a central processing unit ("CPU") 205 that is preferably linked to each of the following elements by means of a shared data bus or by dedicated connections: clock 210, random access memory ("RAM") 215, read only memory ("ROM") 220, input/output ("I/O") communications port 225 and a plurality of databases 230.

The CPU 205 performs all of the processing functions of the central server 200 in accordance with a stored operating system ("OS"; not shown) having multi-tasking capabilities.

Because the system is intended for access by a large number of users, healthcare service providers 120 and sponsors 130 asychronously, the RAM 215 is preferably of sufficient size to prevent problems such as slow loading and system failure due to too many connections being attempted to be established at the same time. Furthermore, the I/O communications port 225 must be configured to include multiple communications channels for simultaneous connections, and may be stand-alone devices.

The central server 200 indirectly communicates with the customers on hypertext transfer protocol ("HTTP") that is secured using a standard secure protocol (e.g., secure socket layer ("SSL")) through the input/output communications port 225. As previously mentioned, the customers gain access to the Internet 140 by means of their ISP's. When the customers request access to the Web site associated with the central server 200 by transmitting the Web site's registered domain name (e.g., "BuyMedDirect.Com"), the customers' requests are routed through their ISP's to a second ISP (not shown) associated with the central server 200. The second ISP in turn routes the customers' requests to the central server's I/O communications port 225 via a communication line, such as a dedicated phone line (e.g., a T1 or T3 line). This type of line provides a high-speed data connection between the second ISP and the central server 200.

The central server 200 also includes certain software components, such as software servers and software databases, to store information and perform a plurality of transactions. The implementation of software servers to execute Internet-directed software in conjunction with a central server is well-known in the art, and the servers' configurations are accordingly not described in detail herein.

Because the system is configured in a preferred embodiment to provide tailored, customer-specific banner advertisements, the CPU 205 is also in communication with one or more input device 235, such as a keypad and a scanner, to receive the advertisements and their parameters for storage. The central server 200 could alternatively receive this information from advertisers over the Internet 140.

The plurality of databases 230 will now be described in detail below. With respect to the databases 230, it should be noted that each database in the figures is shown to have only a few records contained therein for purposes of illustration, although it should be understood that in practice each database would contain numerous records. Furthermore, it should be understood that the invention is not limited to the fields illustrated in the figures and that fields could be added, replaced or deleted without departing from the scope and spirit of the invention.

Databases

A registration database 1000 tracks log-in names, passwords and other relevant information for identifying and authenticating registered users, healthcare service providers and sponsors into the Web site associated with the central server 200. As shown in FIG. 10, the registration database 1000 maintains a plurality of records, such as records 1050 to 1090, with each record being associated with a registrant identified by a log-in identifier stored in field 1005 and a password stored in field 1010. The registrant's preference ("yes" or "no") with respect to "cookies", a term referring to the storage of the log-in identifier at the registrant's computer for being automatically provided to the server 200 upon access to the Web site, is stored in field 1015. Other relevant information, such as the registrant's e-mail address, home ZIP code, and categorization ("U" for user 110; "HP" for healthcare service provider 120; "S" for sponsor 130) are stored in fields 1020, 1025, and 1030 respectively.

A sponsoree database 1100 stores information regarding the user's "sponsor", i.e., the entity/individual responsible for paying for all or part of the user's healthcare services package. Referring to FIG. 11, the sponsoree database 1100 maintains a plurality of records, such as records 1150, 1160 and 1170, with each record being associated with a user 110 identified by the log-in identifier stored in field 1105. The user's ZIP code is stored in field 1110. The type of sponsor ("U" for the user 110; "E" for employer; or "H" for HAC, e.g., insurance company, HMO, or Third Party Administrator) is stored in field 1115. A sponsor identification code that identifies the sponsor is stored in field 1120 and a sponsoree identification code that identifies a sponsored user (or "sponsoree") is stored in field 1125. Finally, the total number of sponsored individuals associated with the sponsoree and the sponsoree's budget is stored in fields 1130 and 1140, respectively.

A member demographics database 1200 stores information about the user 110 and his family. Referring to FIG. 12, the user demographics database 1200 maintains a plurality of records, such as records 1250, 1260 and 1270, with each record being associated with a user 110 identified by the user's log-in identifier stored in field 1205. The name of the user 110 (First/Middle/Last), member identification number, panel identification number and date of birth (MM/DD/YYYY) are stored in fields 1210, 1211, 1213 and 1215, respectively. The member's social security number, if captured in a preferred embodiment of FIG. 21 (described below), is stored in field 1220 and relationship to the user 110 ("SELF," "SPOUSE," "CHILD" or "OTHER") is stored in field 1225. The member's gender ("M" for male or "F" for female) is stored in field 1230. Lastly, the member's sponsoree identification number is stored in field 1240.

A healthcare service provider database 1300 is shown that stores information regarding participating healthcare service providers. Referring to FIG. 13, the healthcare service provider database 1300 maintains a plurality of records, such as records 1360, 1370 and 1380, with each record being associated with a healthcare service provider 120 identified by the log-in identifier stored in field 1305. The healthcare service provider's category, service type and provider identification number are stored in fields 1310, 1315 and 1320, respectively. The beginning effective date and ending effective date of the provider's offered services are stored in fields 1325 and 1330. The provider's rate type ("P" for Pre-paid or "F" for Fee-for-Service) is stored in field 1335, and a Pre-paid Month's Notice and a Fee-For-Service Month's Notice are stored in fields 1340 and 1345, respectively. A separate record is created for the healthcare service provider 120 for each category of service that the healthcare service provider 120 offers.

A sponsor information database 1400 is shown that stores information regarding the sponsor 130 (or the user 110 if the user 110 is self-sponsored). Referring to FIG. 14, the sponsor information database 1400 maintains a plurality of records, such as records 1450, 1460 and 1470, with each record being associated with a sponsor 130 identified by the sponsor's log-in identifier stored in field 1405. The sponsor's name and address are stored in fields 1410 and 1420, respectively. A contact name, phone number and e-mail address for the sponsor 130 are stored in fields 1425, 1430 and 1435, respectively. The type of sponsor ("E" for Employer, "H" for HAC, "S" for Self, "O" for Other) is stored in field 1440. Finally, the sponsor's identification code is stored in field 1445.

A sponsored individual database 1500 is shown that stores information regarding sponsored users (or "sponsorees").

Referring to FIG. 15, the sponsored individual database 1500 maintains a plurality of records, such as records 1550, 1560 and 1570, with each record being associated with a sponsored user identified by the sponsor's identification code stored in field 1505. A sub-sponsor identifier is stored in field 1510, and a sponsoree identification number and a sponsoree name are stored in fields 1515 and 1520, respectively. The budgeted contribution for the sponsoree is stored in field 1525, and the sponsoree's initial password for accessing the record associated with the sponsoree is stored in field 1530. A separate record is created for each sponsoree of the sponsor 130.

A CPT database 1600 is shown that stores information regarding Current Procedural Terminology ("CPT") codes, which are standard healthcare industry categorization codes for physician services that have been developed and copyrighted by the American Medical Association. Referring to FIG. 16, the CPT database 1600 maintains a plurality of records, such as records 1650, 1660 and 1670, with each record being associated with a log-in identifier stored in field 1605. The healthcare service provider's identification number and category of service are stored in fields 1610 and 1615, respectively. The CPT code and the established beginning effective date and ending effective date for the CPT code associated with that particular healthcare service provider 120 are stored in fields 1620, 1625 and 1630, respectively. A separate record is created for each category and CPT code combination of the healthcare service provider 120.

A physician background database 1700 is shown that stores information regarding a physician's background, training and the like. Referring to FIG. 17, the physician background database 1700 maintains a plurality of records, such as records 1750, 1760 and 1770, with each record being associated with a physician identified by its log-in identifier stored in field 1705. The physician's name, education/training and board certifications are stored in fields 1710, 1715 and 1720, respectively. The physician's office location, office hours and associated partners in the physician's medical group are stored in fields 1725, 1730 and 1735, respectively. Finally, the physician's provider identification number is stored in field 1740.

A rates database 1800 is shown that stores information regarding healthcare service provider rates. Referring to FIG. 18, the rates database 1800 maintains a plurality of records, such as records 1850, 1860 and 1870, with each record being associated with a log-in identifier stored in field 1805. The provider's identification number and category are stored in fields 1810 and 1815. The provider's rate type ("P" for Pre-paid or "F" for Fee-for-Service) is stored in field 1817. An age category and a monthly rate for males for the age category and monthly rate for females for the age category are stored in fields 1820, 1825 and 1830, respectively. The co-payment amount associated with the provider's rate is stored in field 1835. Lastly, the provider's beginning effective date and ending effective date for the rates are stored in fields 1840 and 1845. For each age category and co-payment combination for which a provider is offering a rate, there will be a separate record in the rates database 1800.

A referral database 1900 is shown that stores information regarding healthcare service provider referrals. Referring to FIG. 19, the referral database 1900 maintains a plurality of records, such as records 1950, 1960, 1970, 1980 and 1990, with each record being associated with the healthcare service provider's log-in identifier stored in field 1905. The healthcare service provider (or "referrer") identification number is stored in field 1908. The referrer's beginning effective date and ending effective date for each referral are stored in fields 1910 and 1915, respectively. The referree's category, name and provider identification number are stored in fields 1920, 1925 and 1930, respectively. Finally, the healthcare service provider's referral panel identification number is stored in field 1935. A separate record is created for each combination of referrer provider identification, provider name and category in the referral database 1900.

A member panel database 900 is shown that stores information regarding the member's selected healthcare services panel. Referring to FIG. 9, the member panel database 900 maintains a plurality of records, such as records 950, 960 and 970, with each record being associated with a member identifier stored in field 905. The member's name and panel identification number are stored in fields 907 and 908. The member's selected category, associated provider identification number and co-payment are stored in fields 910, 915 and 920, respectively. The member's rate type ("P" for Pre-paid or "F" for Fee-for-Service) and rate are stored in fields 923 and 925, respectively. Lastly, the beginning effective date and ending effective date for the member's rates are stored in fields 930 and 935, respectively. A separate record is created in the member panel database 1900 for each category of service selected by the member.

An embodiment of a process for the system described above will now be discussed below. Unless otherwise indicated, the processes are described from the viewpoint of the central server 200.

Registration Process

Figure 3A:
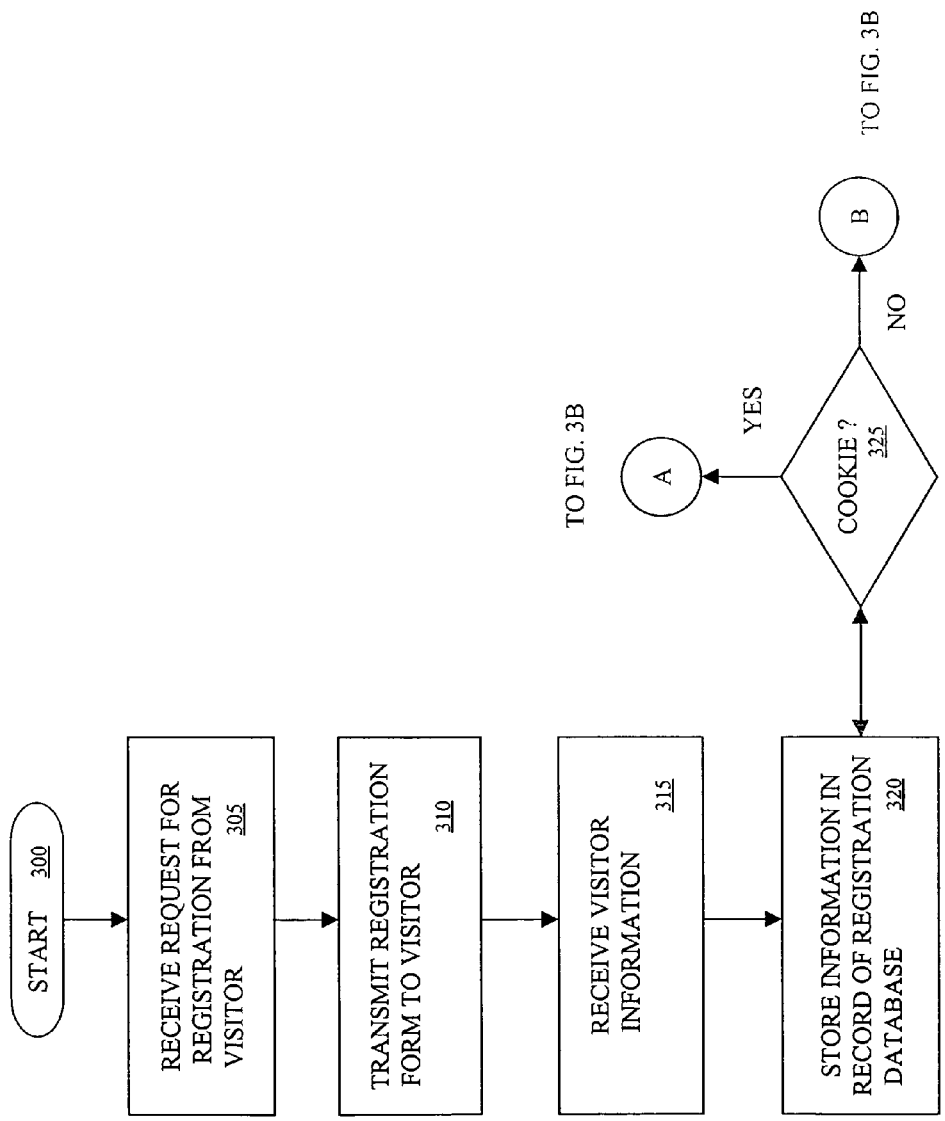
FIGS. 3A-3C are flow diagrams illustrating an embodiment of a registration process.
Figure 3B:
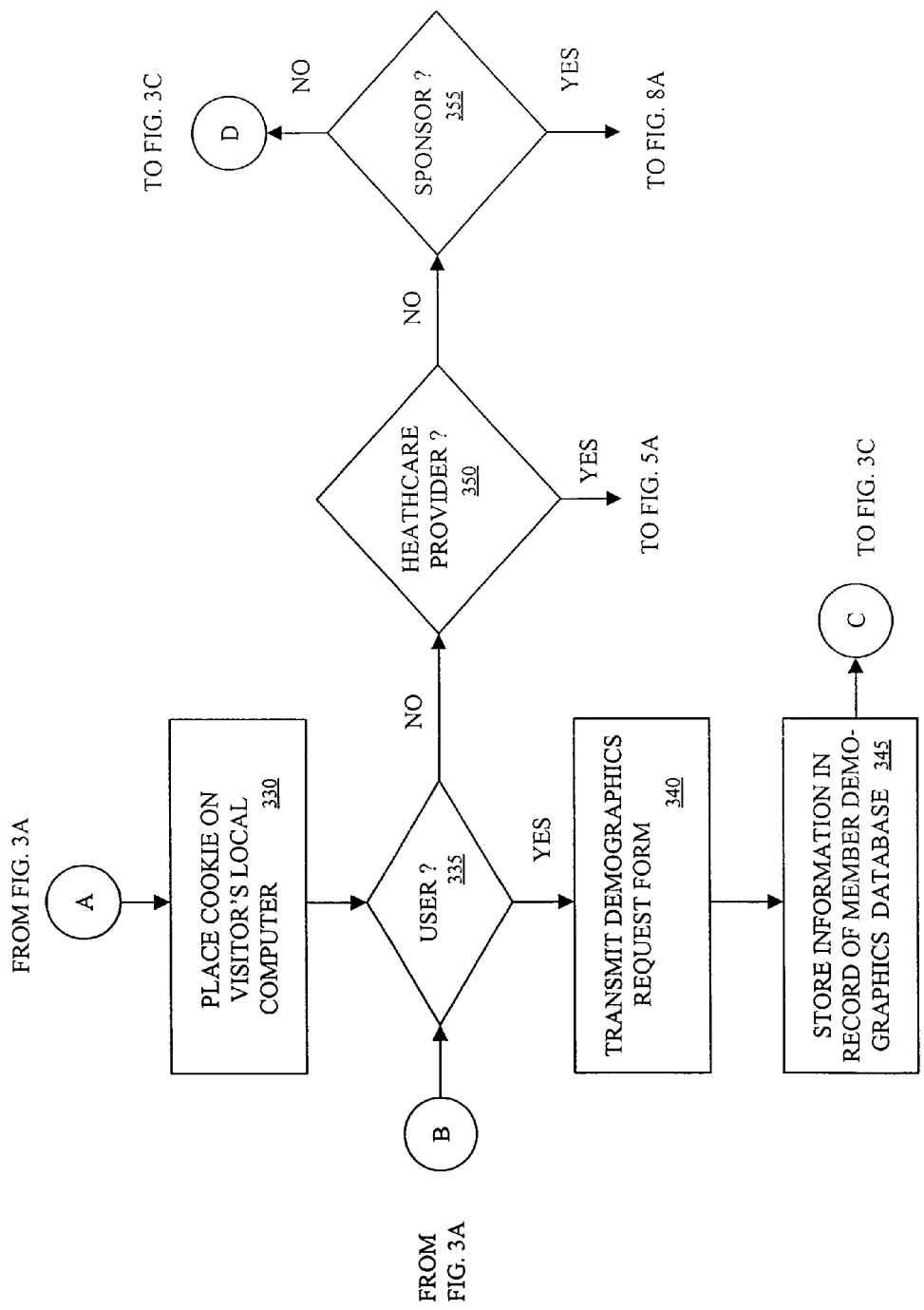
Figure 3C:
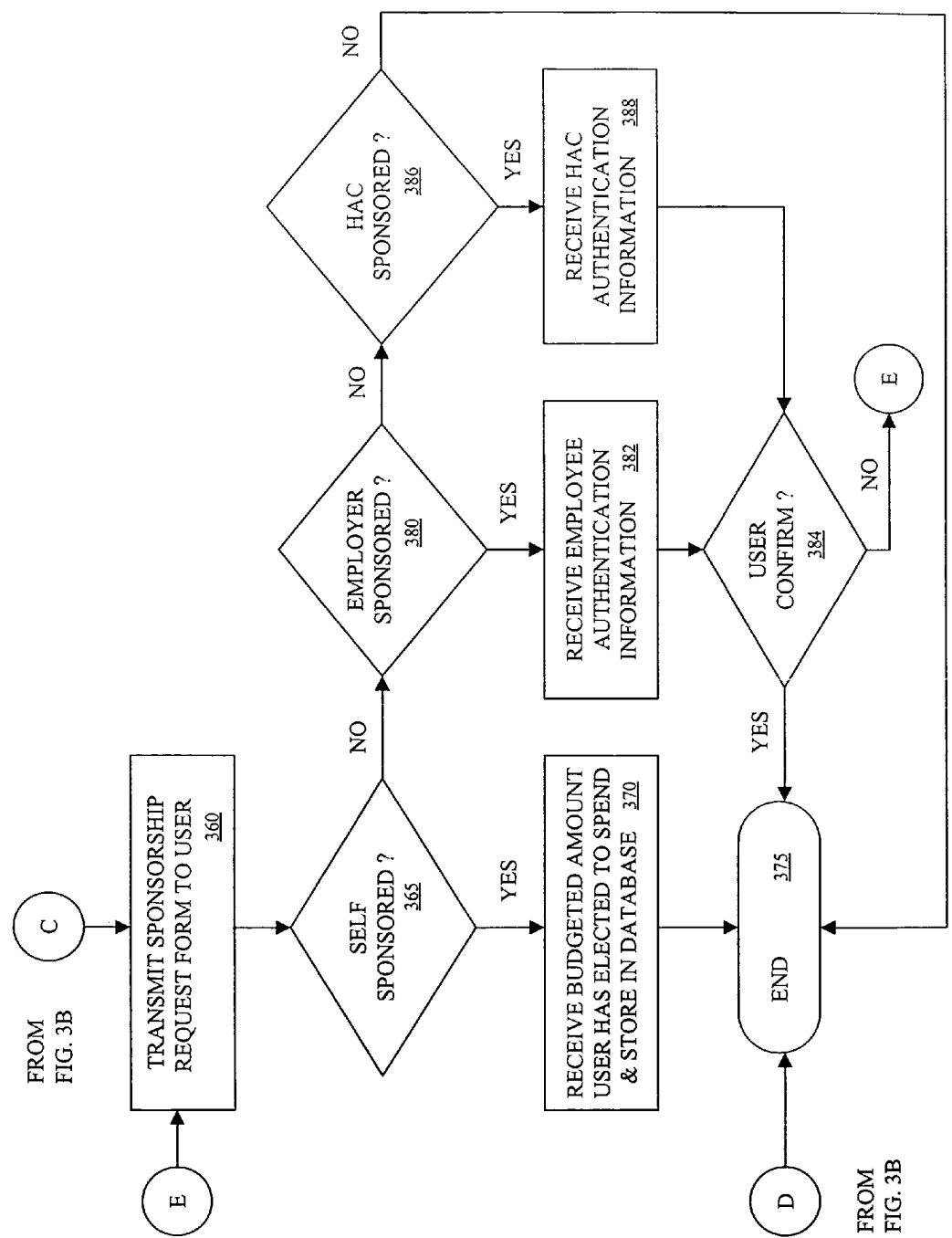
Figure 4A:
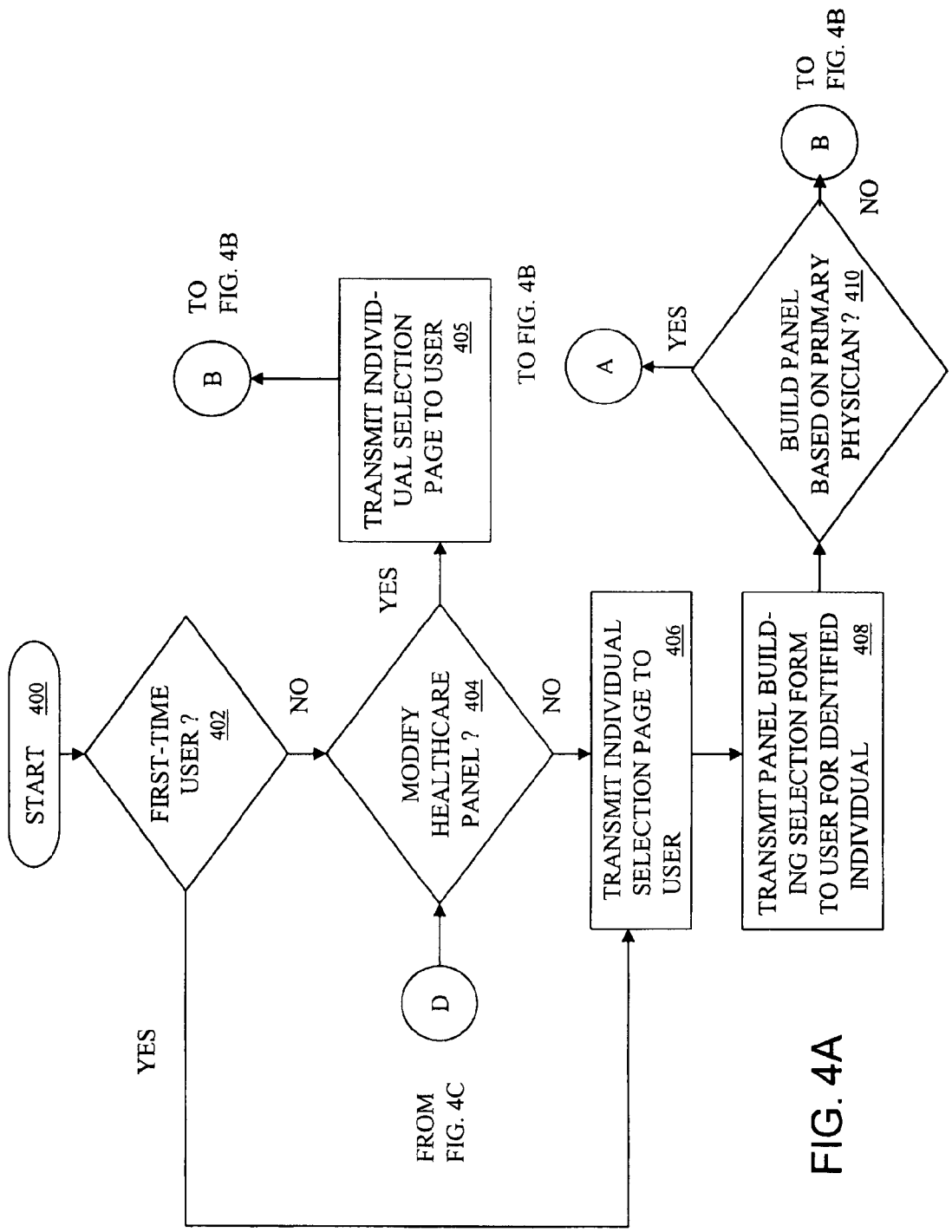
FIGS. 4A-4D are flow diagrams illustrating an embodiment of a healthcare services panel selection process.
Figure 4B:
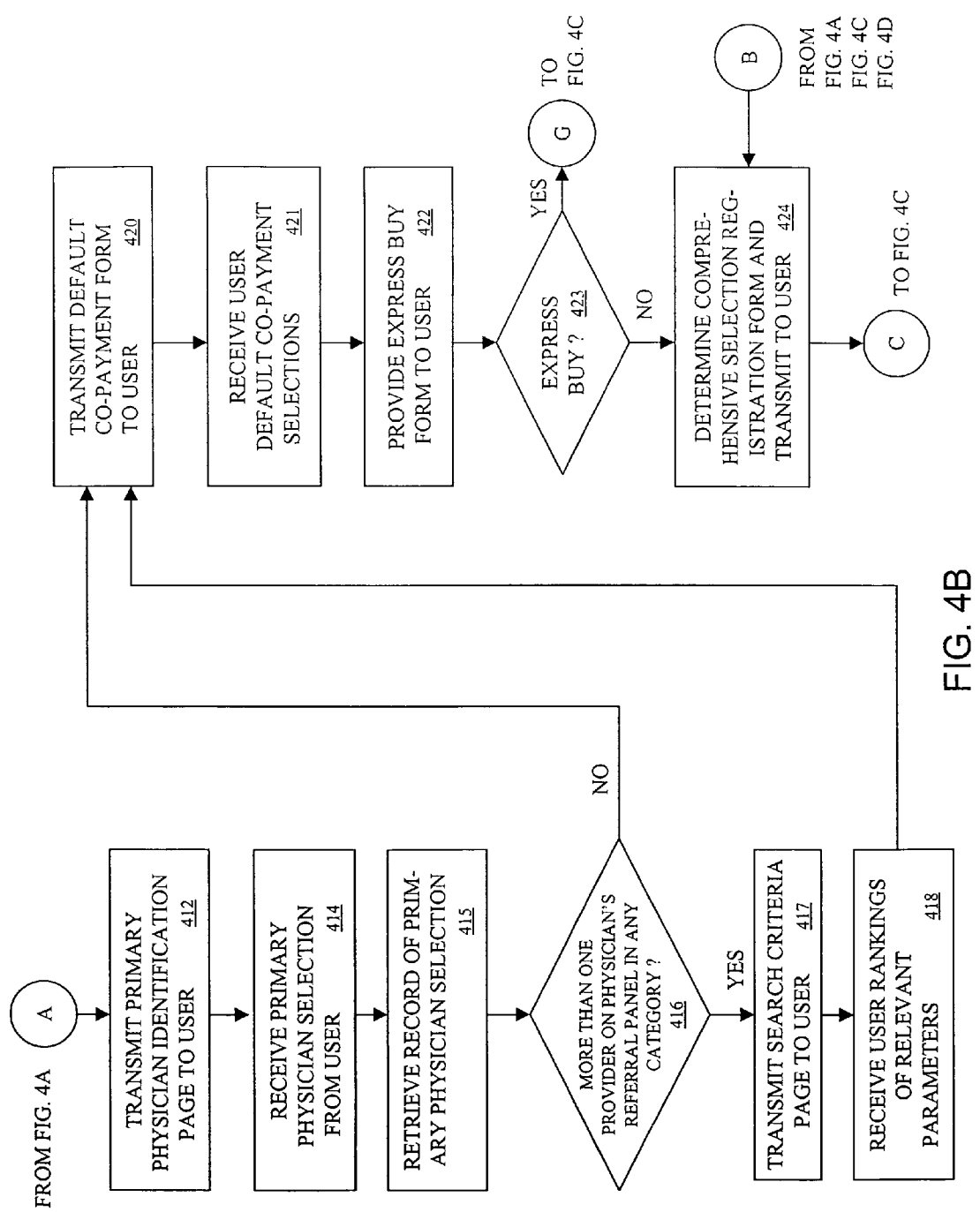
Figure 4C:
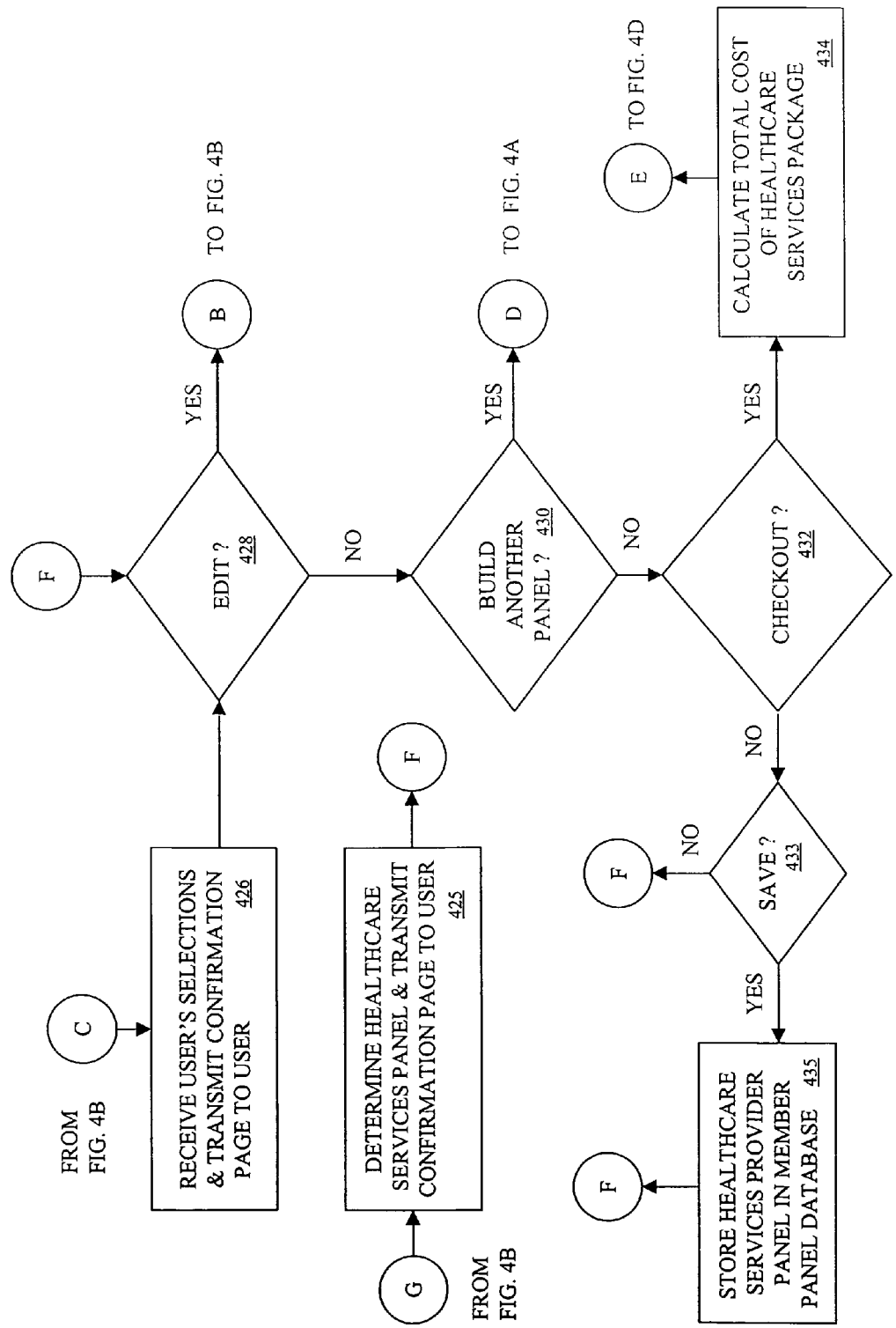
Figure 4D:
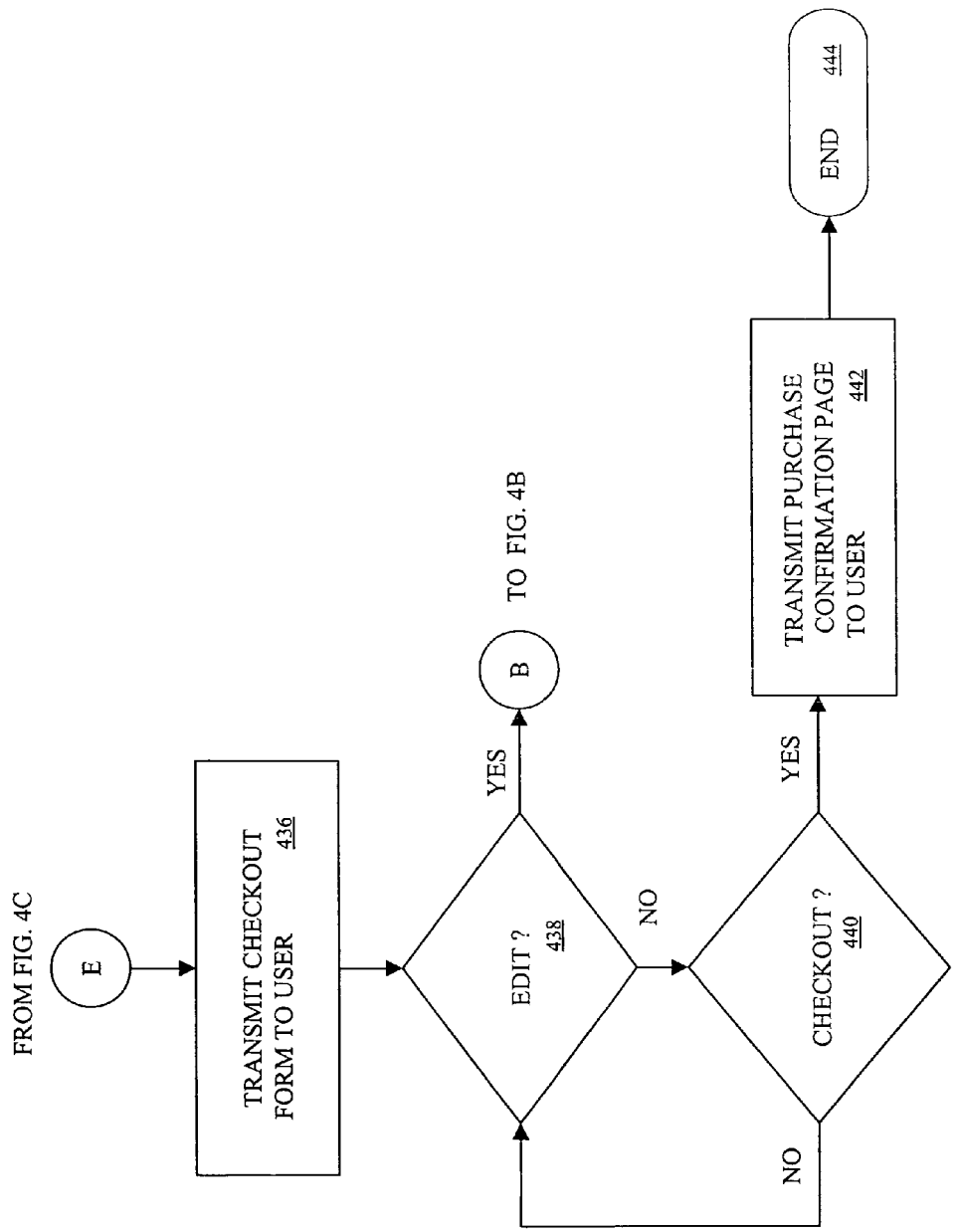

Referring to FIGS. 3A-3C, the registration process for a first-time visitor begins at step 300. In step 305, a request for registration from the visitor is received over the Internet 140 via the system's Web site. In response, a registration form is transmitted back to the visitor in step 310 for input by the visitor of a log-in identifier (or "User ID"), password, e-mail address, home ZIP code, indication of his cookie preference and an indication of whether the visitor is a consumer/purchaser (and, if so, the number of family members to be associated with his account), healthcare service provider (e.g., physician or hospital) or sponsor (e.g., employer or insurance carrier). An example of a registration form is illustrated in FIG. 20.

Referring to FIG. 20, the options "Next" and "Previous" are provided to the registrant on the bottom of the form for selection. These options are also present in a number of other forms illustrated in the figures. As used throughout the specification and figures, a selection of "Next" by the registrant, user 110 or other individual accessing the system indicates a transmission of information on the form back to the central server 200. A selection of "Previous" loads the previous form or page that was displayed and accordingly repeats the process beginning at the step associated with the transmission of that form or page. In a preferred embodiment, if the option "Next" is selected and information is missing from required fields or entered in an incorrect format, an error message will be displayed and the form will be re-transmitted indicating which field(s) require information to be inserted or changed.

Upon receipt of the information on the registration form from the visitor in step 315, a record is created for the visitor in the registration database 1000 and the information is stored in the appropriate fields of the record in step 320. For example, registration information regarding the visitor "john_jones", a user 110, is stored in record 1050 of the registration database 1000. In step 325, a determination is made whether or not the visitor has indicated that he would like a cookie to be placed on his local computer by reference to field 1015 of the created record. If so, in step 330 a cookie is placed on the visitor's local computer that will indicate the log-in identifier when the visitor re-accesses the Web site at a later time. The use and placement of cookies is well-known in the art, and accordingly will not be described herein in detail.

Figure 21:
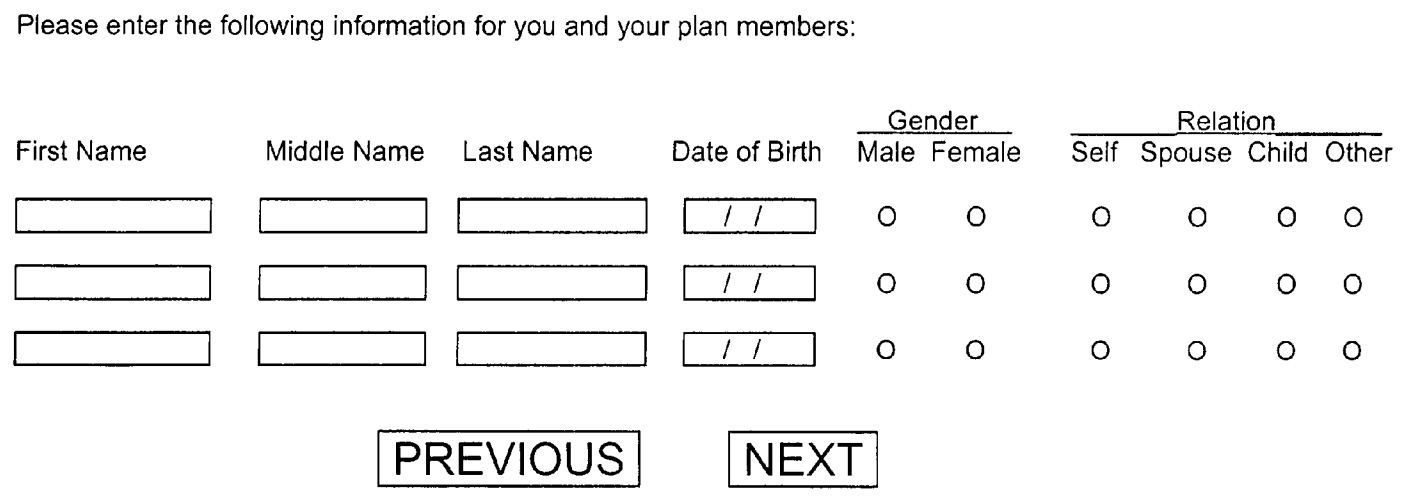

In step 335, it is determined whether the visitor is a user 110 by reference to field 1030 of the registration database 1000 (e.g., "Consumer/Purchaser" was selected on the registration form of FIG. 20). If so, a demographics request form is transmitted to the user 110 is step 340. An example of a demographics request form is illustrated in FIG. 21. The purpose of the demographics request form is to receive information from the user 110 regarding the names, birth dates, gender and relation to the user 110 of all the individuals to be associated with and included in the user's healthcare services package. As will be discussed in more detail below, this information can be used to determine the individuals' rates corresponding to the healthcare service providers selected by the individuals to be included on their healthcare services panels. Although not shown in FIG. 21, in a preferred embodiment the demographics request form further contains a field to receive the individuals' social security numbers.

Figure 5A:
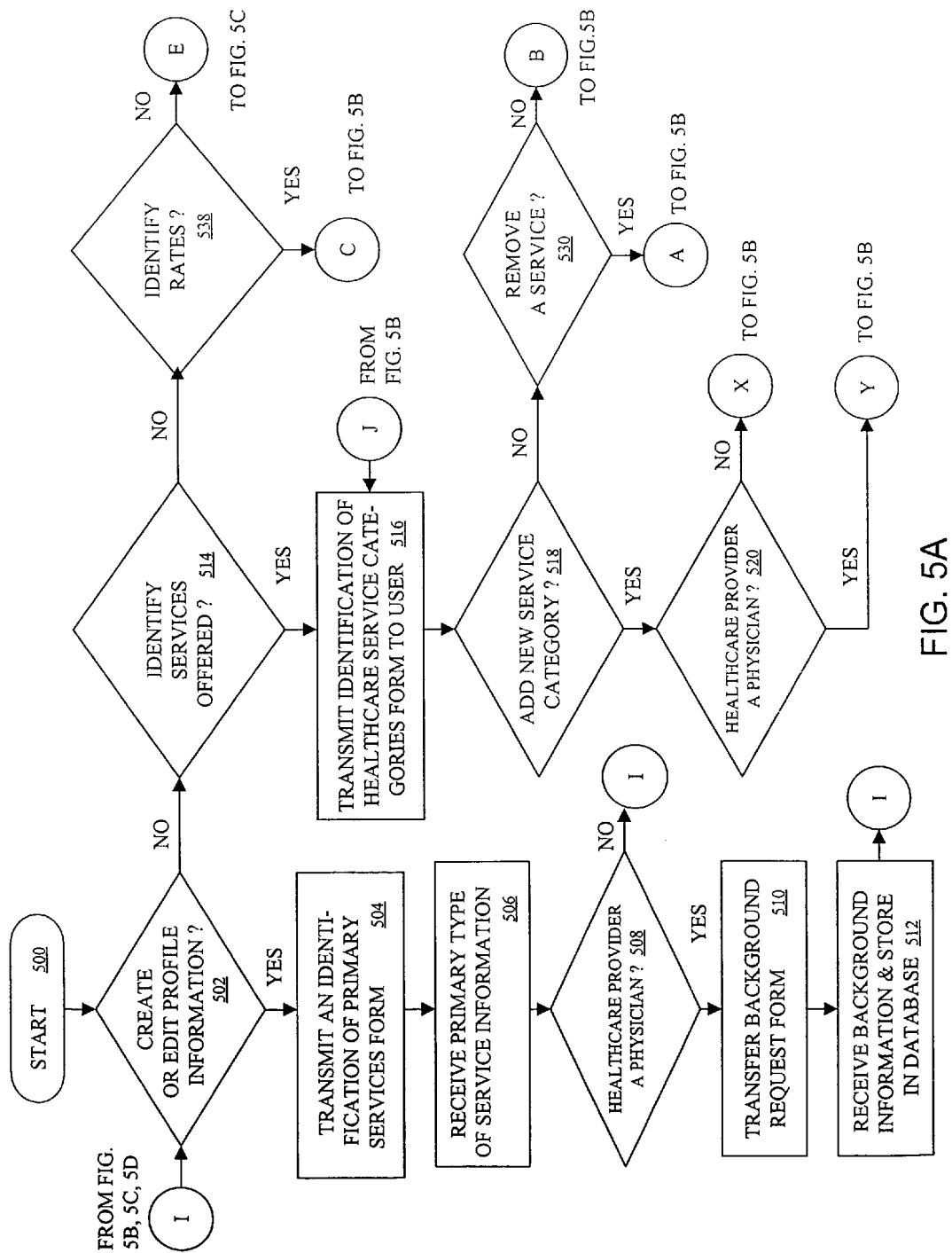
FIGS. 5A-5D are flow diagrams illustrating an embodiment of a healthcare service provider registration process.
Figure 5B:
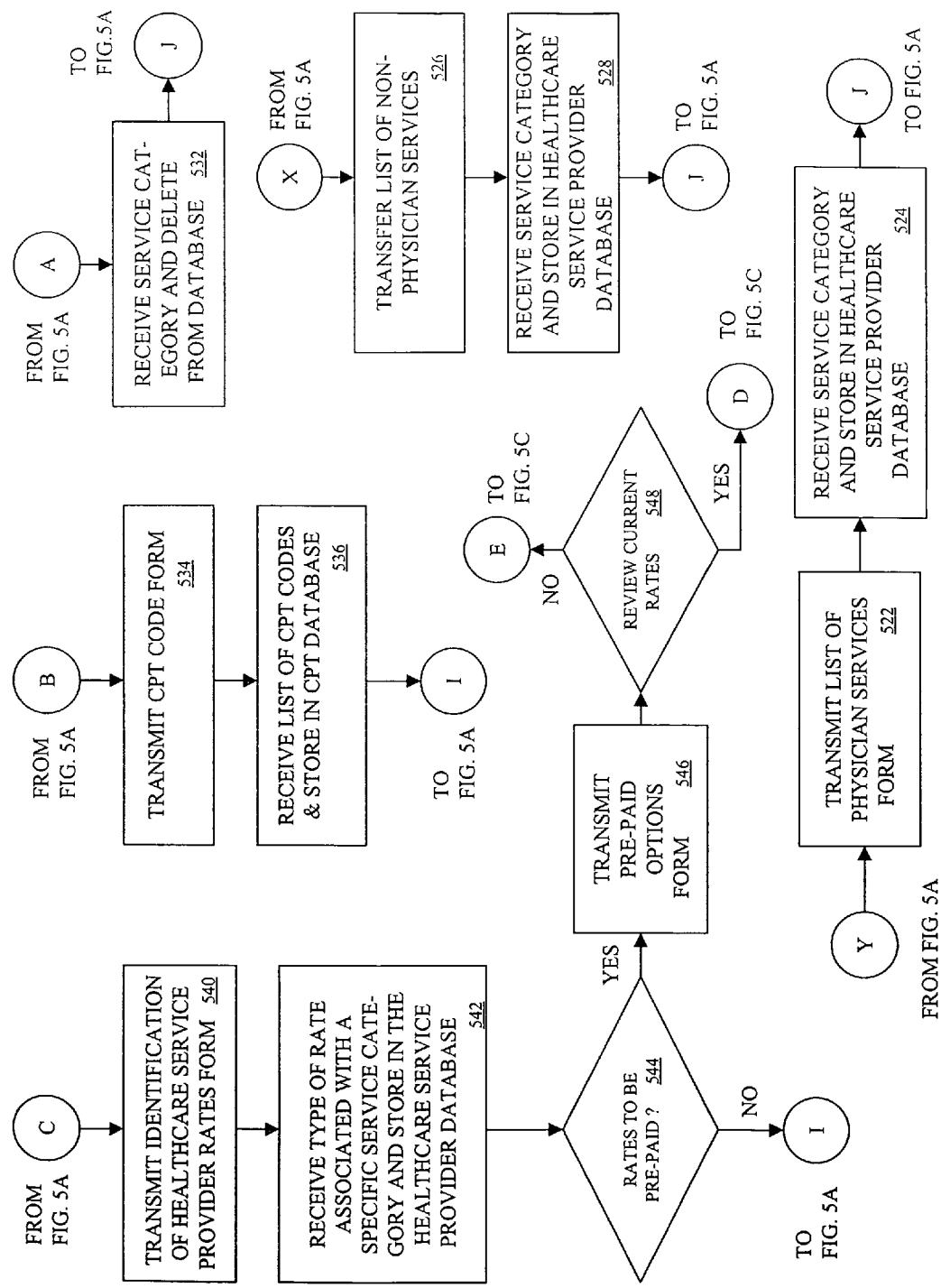
Figure 5C:
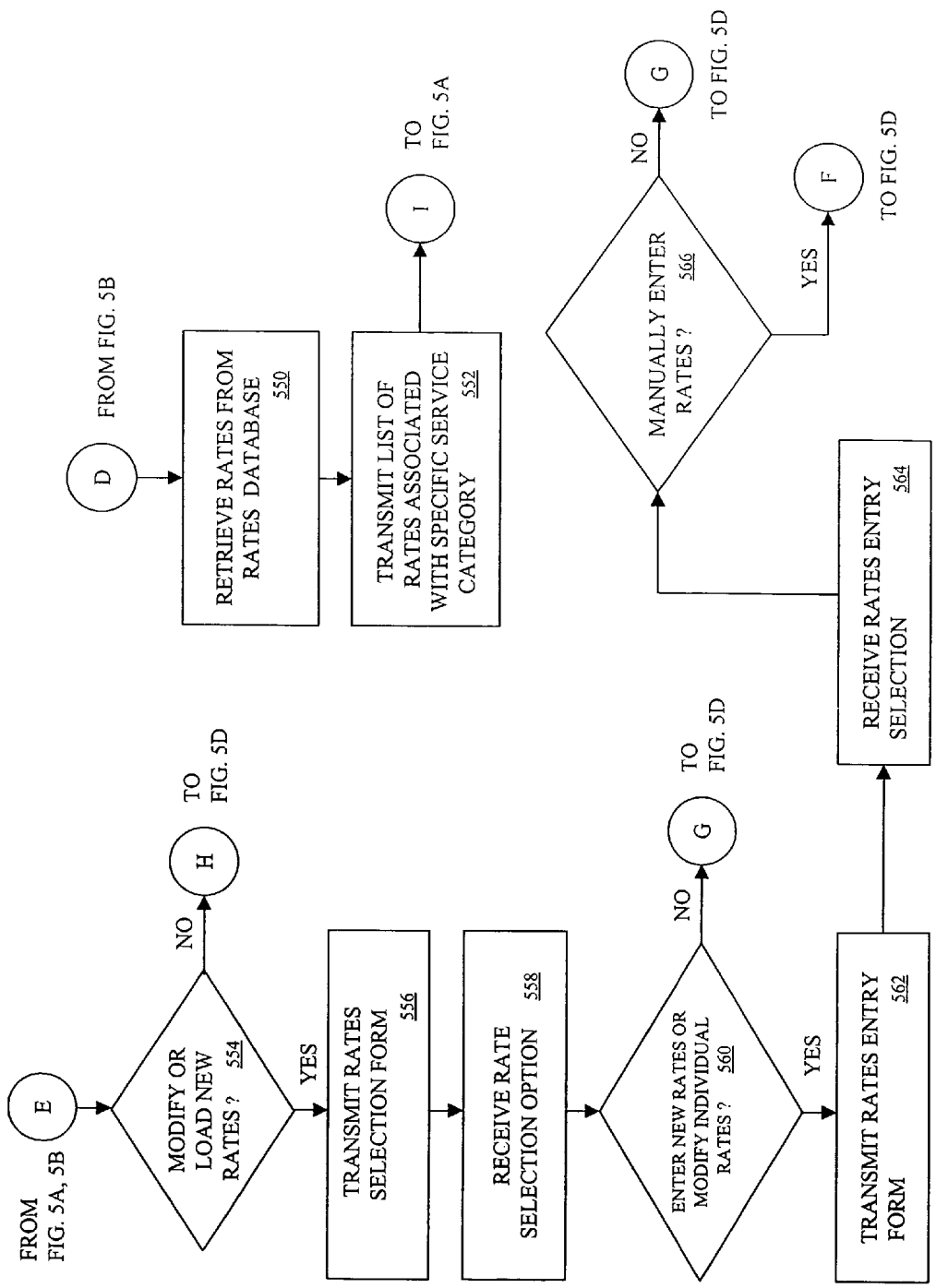
Figure 5D:
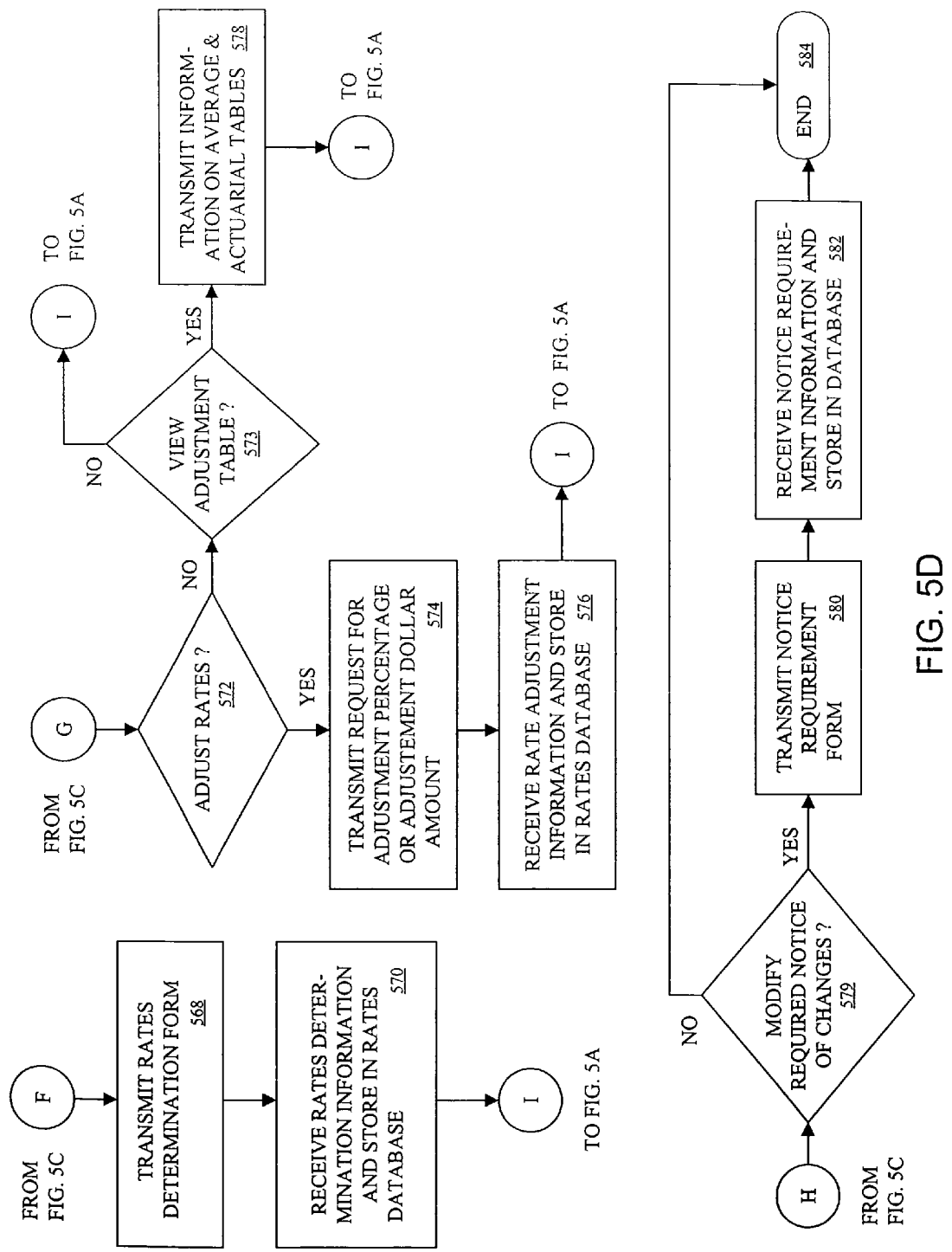
Figure 8A:
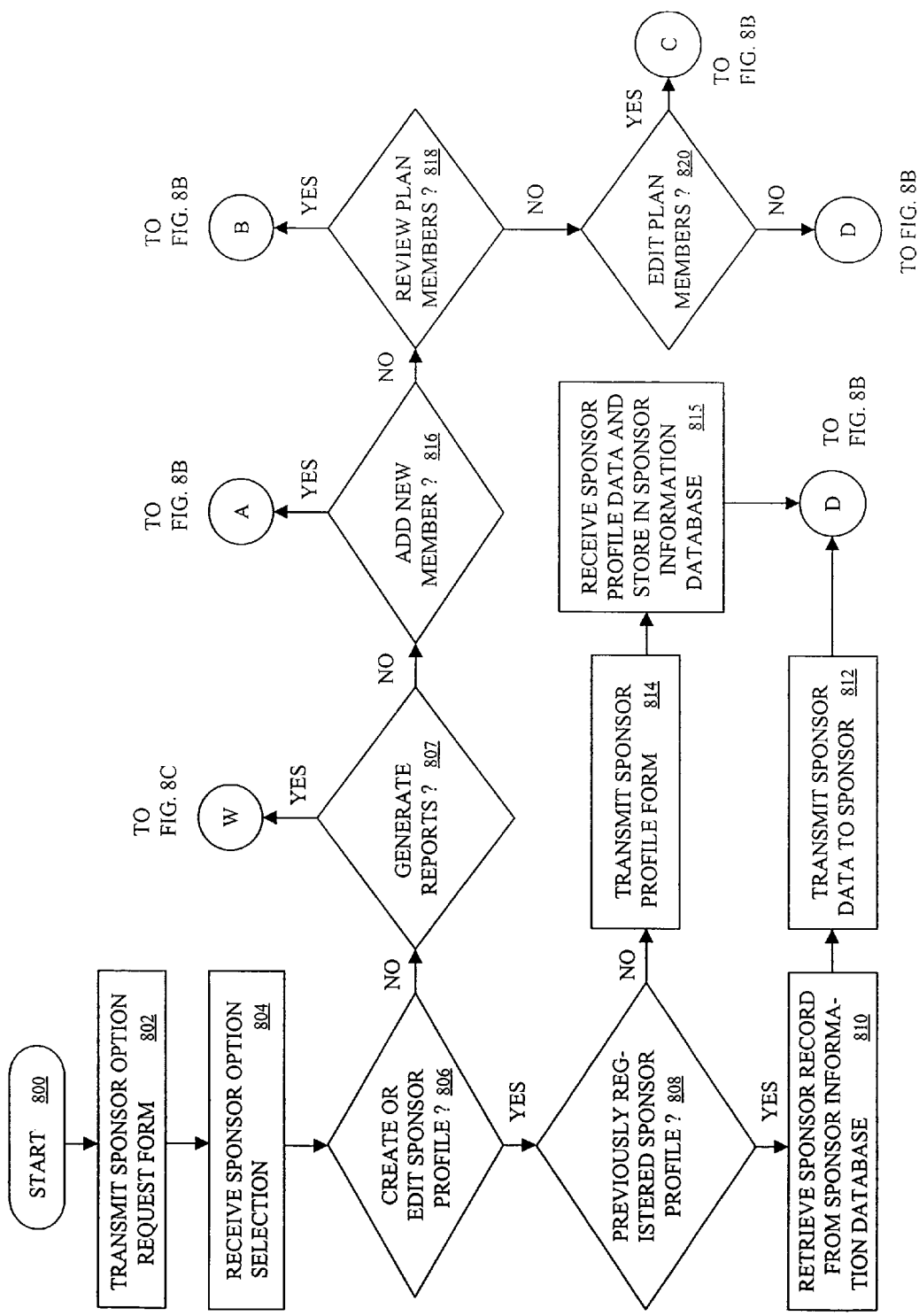

If it is determined that the visitor is not a user 110, but is either a healthcare service provider (step 350) or a sponsor (step 355), the process continues as described and set forth in detail below with respect to FIG. 5A or 8A, respectively.

Upon receipt of the demographics information from the user 110, in step 345 a record identified by the user's log-in identifier is created for each individual (or "member") associated with the user 110 in the member demographics database 1200, and the demographics information is stored in the appropriate fields. For example, the name (field 1210) and birthdate (field 1215) of "John Michael Jones" are stored in record 1250; the name (field 1210) and birthday (field 1215) of his spouse, "Jenny Lee Jones", are stored in record 1260; and the name (field 1210) and birthday (field 1215) of his child, "Julia Lynn Jones", are stored in record 1270 (along with the sponsoree identifier 1240, as retrieved from the sponsoree database 1100). All of the records are identified by the log-in identifier "john_jones" in field 1205.

In step 360, a sponsorship request form is transmitted to the user 110 for determining the user's sponsor, i.e., the entity responsible for paying all or part of the user's healthcare benefits. An example of a sponsorship request form is illustrated in FIG. 22. In step 365, it is determined whether the user 110 is self-sponsored (e.g., has selected the option "Self" on the sponsorship request form) and has elected a budgeted amount of money annually to spend on a healthcare services package. The user 110 may elect to spend nothing ("0") if the user 110 is soliciting a price estimate. In step 370, a record is created identified by the user's log-in identifier in field 1105 of the sponsoree database 1100 and the type of sponsor ("U" for user 110 in the event that the user is self-sponsoring his program) and the budgeted amount the user 110 has elected to spend is stored in fields 1115 and 1140, respectively (along with the user's ZIP code and number of family members, as retrieved from the registration database 1000).

If it is determined in step 365 that the user 110 is not self-sponsored, a determination is made whether the user 110 is employer-sponsored in step 380 (e.g., the user 110 has selected the option "Employer" on the sponsorship request form of FIG. 22). If the user 110 is employer-sponsored, an employer identification request form is transmitted to the user 110 for input of the user's employer (i.e., sponsor) identification code, employee (i.e., sponsoree) identifier, and employee (i.e., sponsoree) identifier password (hereinafter "employer authentication information"). An example of an employer identification request form is illustrated in FIG. 23.

If the employee does not know or remember his employer's identification code, in a preferred embodiment the sponsor information database 1400 is searchable by the employee to obtain this information.

Upon receipt of the employer authentication information in step 382, the matching record containing the sponsoree's name (field 1520), sponsor identification code (field 1505), sub-sponsor identification code (field 1510), sponsoree identifier (field 1515), contribution (field 1525) and the user's initial password (field 1530) is retrieved from the sponsored individual database 1500 as identified by the employer authentication information and an employer confirmation page transmitted to the user 110 for confirmation. An example of an employer confirmation page for the user "John Michael Jones", whose employer Wizig & Company contributes $5,000.00 per year to his healthcare services package, is illustrated in FIG. 24.

If there is no matching record as to all required fields and the user's employer is therefore not authenticated, the user 110 will be displayed an error screen where he will be allowed to re-enter his employer authentication information. In a preferred embodiment, for security reasons the user 110 will only be allowed a limited number of attempts to re-enter his information before he is shut out of the system.

If it is determined in step 380 that the user 110 is not employer-sponsored, a determination is made whether the user 110 is HAC sponsored in step 386 (e.g., the user 110 has selected the option "Insurer, HMO or other Healthcare Administrator" on the sponsorship request form of FIG. 22). If the user 110 is HAC sponsored, a HAC identification request form (not shown; similar to the employer identification request form) is transmitted to the user 110 for input of the user's HAC (i.e., sponsor) identification code, HAC (i.e., sponsoree) identifier, and HAC (i.e., sponsoree) password (hereinafter, "HAC authentication information"). If the user 110 does not know or remember his HAC's sponsor identification code, in a preferred embodiment the sponsored individual database 1500 is searchable by the user 110 to obtain this information.

Upon receipt of the HAC authentication information in step 388, the matching record containing the sponsoree's name (field 1520), sponsor identification code (field 1505), sub-sponsor identification code (field 1510), sponsoree identifier (field 1515), contribution (field 1525) and the users initial password (field 1530) is retrieved from the sponsored individual database 1500 as identified by the HAC authentication information and an HAC confirmation page transmitted to the user 110 for confirmation. The HAC confirmation page is similar to the employer confirmation page, and is accordingly not illustrated herein.

If there is no matching record as to all required fields and the user's HAC is therefore not authenticated, the user 110 will be displayed an error screen where he will be allowed to re-enter his HAC authentication information. As with the employer authentication information described above, in a preferred embodiment the user 110 will only be allowed a limited number of attempts to re-enter his information before he is shut out of the system for security reasons.

In step 384, it is determined whether the user 110 has confirmed the information provided to the user 110 on either the employer or HAC confirmation forms. If so, the registration process ends in step 375 and the confirmed sponsor identification code, sponsoree identification number and budget information is stored in fields 1120, 1125, and 1140, respectively, of a record created in the sponsoree database 1100 (in addition to the user's log-in identifier, ZIP code and number of individuals on his account, as retrieved from the registration database 1000). If not, the sponsorship information request process repeats beginning at step 360 until the process ends.

Healthcare Services Panel Selection Process

The healthcare services panel selection process will now be described with reference to FIGS. 4A-4D, beginning at step 400.

In step 402, the user 110 is requested to identify whether he is a first-time user. If it is determined that the user 110 is not a first-time user, the user 110 is requested to select whether he would like to make modifications to his healthcare services panel by using previous selections in step 404. If the user 110 does not want to use his previous selections, or if the user 110 is a first-time user, an individual selection form is transmitted to the user 110 requesting the user 110 to identify the person for whom the user 110 will build a healthcare services panel in step 406. An example of an individual selection form for "John Michael Jones" and his family is illustrated in FIG. 25.

In step 408, a panel building selection form is transmitted to the user 110 for an indication by the user 110 of how to build a healthcare services panel for the identified individual, e.g., built around a Primary Physician, built around a chosen hospital, by lowest cost or by building a customized panel. An example of a panel building selection form for the selected individual, "Jenny Lee Jones," is illustrated in FIG. 26. As used in the specification and claims, the entity around which the user 110 selects to build a healthcare services panel for an identified individual (e.g., a Primary Physician or a chosen hospital) is referred to as an "anchor provider".

In step 410, it is determined whether the user 110 has selected to build the healthcare services panel based on the individual's Primary Physician. If so (e.g., the user 110 has selected "Let me start with a panel built around my chosen Primary Physician"), a Primary Physician identification form is transmitted to the user 110 in step 412. An example of a Primary Physician identification form is illustrated in FIG. 27.

The Primary Physician can be any type of physician (e.g., cardiologist, oncologist, nephrologist, internist) and is not limited to PCPs. As shown in FIG. 27, the user 110 has the option to either select a Primary Physician from a drop down menu or by searching the physician background database 1700, rates database 1800, and referral database 1900 according to criteria such as the Primary Physician's name, ZIP code, distance from the user 110, value, price or hospital affiliation. Software for determining the distance between two addresses is well-known and will be utilized in the preferred embodiment to calculate the distance from the user 110 and the Primary Physician. In a preferred embodiment, the user 110 can also select "More Information" to obtain additional information from the physician background database 1700 about the selected Primary Physician. The user's Primary Physician selection is received in step 414.

The record containing the Primary Physician's previously entered selections of the Primary Physician's referral panel (e.g., physicians, hospitals, skilled nursing facilities, and laboratories) is retrieved from the referral database 1900 in step 415 and if it is determined in step 416 that the Primary Physician has more than one healthcare service provider on its referral panel in at least one healthcare service provider category, a search criteria form with criteria for sorting the Primary Physician's selections within the appropriate healthcare service provider categories is transmitted to the user 110 in step 417. An example of a search criteria form is illustrated in FIG. 28. The purpose of the search criteria form is to sort a Primary Physician's list of healthcare service providers based on user-selected criteria if more than one healthcare service provider is listed for any specific category. As shown in FIG. 28, drop-down menus with options for selection by the user 110 with respect to relevant parameters (e.g., distance from the user 110 in terms of miles, distance from the user 110 in terms of time, value, price, and hospital affiliation) is provided, along with a provision for the selection of a parameters priority to the user 110, which is selected by associating a unique number with each category. For example, if there are five parameters, or searching criterion, the user 110 can associate a parameter's priority by ranking the individual parameter from 1 to 5. The user's selections and rankings of the relevant parameters are received in step 418.

A default co-payment form is next transmitted to the user 110 in step 420. An example of a default co-payment form is illustrated in FIG. 29. The default co-payment form provides the user 110 with the option of selecting a default co-payment from a drop-down menu that is to be automatically loaded into each healthcare service provider category of the comprehensive selection registration form (discussed below), including whether he would like to choose the next lowest or highest co-payment in the event that the amount of the selected default co-payment is not available for a specific healthcare service provider category. The user's default co-payment selection is received in step 421.

In step 422, an express buy form is transmitted to the user 110. An example of an express buy form is illustrated in FIG. 55. The express buy form provides the user 110 with "Express Buy" and "Custom Buy" options. "Express Buy" allows the user 110 to purchase a healthcare services panel based on the search criteria received in step 418. "Custom Buy" allows the user 110 to build a customized healthcare services panel, with the options of express buying, custom buying or excluding services listed in three different categories: Category 1, which contains services that are often custom buy or higher cost items such as those that usually exceed a stipulated percentage of the total cost (e.g., inpatient hospital, pharmacy), Category 2, which contains services that are occasionally custom buy; and, Category 3, which contains services that are infrequently custom buy. If it is determined that the user 110 has elected to "Express Buy" in step 423, the user's selections and ranking of the relevant parameters are used to establish a healthcare services panel for user 110 in step 425. If it is determined that the user 110 has elected to "Custom Buy" in step 423, a comprehensive selection registration form (described below) is determined and transmitted to the user 110 in step 424. The additional information with respect to the three categories described above is received and a healthcare services panel is established for the user 110 based on that information and a confirmation form (also described below) is transmitted to the user 110 in step 426.

An example of a comprehensive selection registration form is illustrated in FIG. 30. The comprehensive selection registration form provides a list of healthcare service providers for each healthcare service provider category in drop-down menus. If there is only one healthcare service provider to be displayed in a specific healthcare service provider category, that healthcare service provider's name is displayed in the window. If there is more than one healthcare service provider to be displayed, the names of the healthcare service providers are provided in ranked order in accordance with the user's search criterion received in step 418 above. If there are no healthcare service providers available for a specific healthcare service provider category or if the user 110 seeks a healthcare service provider who was not identified by the aforementioned search criteria, the user can expand their search by selecting the option "Search" as illustrated in FIG.

30. The user 110 can select to exclude a healthcare service provider category by selecting the word "None" that is displayed in the window. In a preferred embodiment, additional information can be obtained about the category (e.g., services typically included in cardiology) and/or a specific healthcare service provider (e.g., board certifications, educational background, location, etc.) by the user selecting the option "More Info".

For each healthcare service provider displayed in the comprehensive selection registration form, an associated amount of co-payment is provided in a separate drop-down menu. The amount of co-payment for each healthcare service provider category is determined and provided based on the amount of default co-payment received in step 422. If the default co-payment is available for a specific healthcare service provider, it is displayed. If the co-payment is not available and the user 110 opted to pay the next highest or lowest available co-payment, the amount of that co-payment is displayed. If the user 110 did not select either the next highest or next lowest available co-payment, the word "None Selected" is displayed in the window and, before proceeding, the user 110 must select a co-payment for each healthcare service provider category that the user 110 has chosen a healthcare service provider.

The comprehensive selection registration form also displays information about an umbrella policy including the name of the umbrella policy and the deductible/co-payment of the umbrella policy that is determined by user 110 from among the available alternatives approved by the user's sponsor. An "umbrella policy," as the term is used herein, is a policy that generally covers all healthcare services obtained from healthcare service providers that are not specifically selected by the user 110. Partners within a medical group, hospitals within a hospital system or any other healthcare service provider that shares a primary legal entity are typically deemed to be the same healthcare provider for purposes of determination of services covered by the umbrella policy. An amount of deductible, which is the annual maximum amount that the user 110 pays out of pocket for healthcare services is associated with the umbrella policy. For example, referring to FIG. 30, because Jenny Lee Jones has not selected an obstetrician, if she obtains obstetric services, she will have to pay up to $2,000 of her costs out of pocket.

The comprehensive selection registration form also provides a running calculation of the user's total remaining budget and sub-total of the present panel, and calculates the increase or decrease of the running calculation due to the user's last modification to the panel.

If, in step 410, the user 110 selected to customize his healthcare services panel instead of basing it on a Primary Physician (e.g., the user 110 selected "Let me build a customized panel"), the comprehensive selection registration form has the word "None" displayed in all of the windows. In a preferred embodiment, each category is searchable by the user 110 using the same search criteria as described above with respect to the user's selection of a Primary Physician. Although not described in detail herein, in a preferred embodiment, the user 110 is also given the options of building the healthcare services panel around a chosen hospital or around the lowest cost healthcare service provider.

If, in step 404, the user 110 is a returning user and has indicated that he would like to modify a healthcare services panel, the individual selection form is transmitted to the user 110 in step 405, and the selected individual's panel data is retrieved from the member panel database 900 (based on the member identifier and the name of the person for whom the user 110 is modifying the healthcare services panel, stored in fields 1605 and 1607, respectively) and provided in the appropriate fields of comprehensive selection registration form in step 424.

In step 426, the user's healthcare services panel is received and a confirmation page is transmitted to the user 110 listing the user's selections for each category as to the healthcare service provider and co-payment. An example of a confirmation page is illustrated in FIG. 31. The user 110 is provided with the option of editing the panel, saving the panel, building a healthcare services panel for another family member and checking out (i.e., confirming his selections for pricing).

If in step 428, it is determined that the user 110 has selected to edit the healthcare services panel, the process continues beginning at step 424. If not, in step 430 it is determined whether the user 110 has selected to build a panel for another individual. If so, the process continues beginning at step 404. If not, it is determined whether the user 110 has selected to checkout in step 432. If the user has not selected to checkout in step 432, in step 433 it is determined whether the user 110 has selected to save the healthcare services panel. If so, a unique member panel identification number is assigned for each member and the member panel identification number and each of the user's selections for each member is stored in separate records of the member panel database 900 in step 435. For example, panel identification number 2002 has been assigned to Jenny Lee Jones and her selections for Primary Care: Internal Medicine, Dentist, and Opthamology are recorded respectively in records 950, 960, and 970. The process then continues beginning at step 428.

If the user 110 has selected to checkout, the calculation of the total cost of the healthcare services package is performed in step 434. Each healthcare service provider on the healthcare services panel is associated with a monthly individual cost ("IC") which is based on the age and gender of the individual family member, the stated level of co-payment, and on rates and personal information in the rates database 1800. Each healthcare service provider on the healthcare services panel is also associated with an umbrella policy credit ("UPC") which is determined base on the age and gender of the individual family member, the characteristics of the pre-paid healthcare service provider services selected in the healthcare services panel, and the umbrella policy deductible. A monthly uncredited umbrella policy cost is determined based on the age and gender of the individual family member, an amount of deductible on the umbrella policy and the personal information data in the member demographics database 1200. The total cost for each individual family member is calculated based on: (a) aggregating the ICs associated with each healthcare service provider on the healthcare services panel; (b) aggregating the UPCs of each healthcare service provider on the healthcare services panel; (c) calculating the difference between the uncredited umbrella policy cost and the aggregated amount of the UPCs, wherein the difference represents the monthly credited umbrella policy cost; and (d) determining the total monthly cost of the healthcare services package for the individual family member based on the sum of the aggregated ICs and the credited umbrella policy cost. The annual cost of the healthcare services package is obtained by multiplying the monthly cost by twelve (12).

The annual and monthly cost(s) for the user 110 and his family members are transmitted to the user 110 in a checkout form in step 436. An example of a checkout form for Jenny Lee Jones is illustrated in FIG. 32. The checkout form further contains the user's total annual and monthly budgeted contribution (as retrieved from field 1525 of the sponsored individual database 1500), and the monthly and annual balance available, or due, in the user's account by subtracting the user's total healthcare services package costs from the user's budget. The user 110 is provided with the option of either editing a healthcare services panel or checking out.

In step 438, if it is determined that the user 110 elected to edit a specific healthcare services panel, the comprehensive selection registration form for the specific healthcare services panel is displayed to the user 110 and the process repeats from step 424. If in step 440, it is determined that the user 110 has opted to checkout, a purchase confirmation page is transmitted to the user 110 in step 442. An example of a purchase confirmation page for Jenny Lee Jones is illustrated in FIG. 33, comprising a final list of the physicians, hospitals, and other healthcare service providers selected for her, although in a preferred embodiment it also comprises a final list for each family member associated with the user John Michael Jones.

The healthcare services panel selection process thereafter ends in step 444. In a preferred embodiment, the user 110 is provided with the further options of printing the page or returning to the Web site's home page.

Healthcare Service Provider Options Process

The healthcare service provider registration process will now be described with reference to FIGS. 5-7.

If in step 350 of the registration process (described above) it is determined that the registrant is a healthcare service provider 120, a healthcare service provider options form is transmitted to the healthcare service provider. An example of a healthcare service provider options form is illustrated in FIG. 34. Generally, the healthcare service provider 120 is provided the options to: (1) create or update his profile information; (2) identify the services that he offers; (3) review, load or update his rates; (4) load or update his referral list; and (5) generate reports. Options (1)-(3) (i.e., the healthcare service provider registration process) will be discussed below with respect to FIGS. 5A-5D, option (4) will be discussed below with respect to FIGS. 6A-6B, and option (5) will be discussed below with respect to FIGS. 7A-7B.

Referring now to FIGS. 5A-5D, a healthcare service provider registration process begins in step 500.

Create/Edit Profile

In step 502, if it is determined that the healthcare service provider 120 has selected to create or edit his profile (e.g., has selected the option "Profile Information" of the healthcare service provider options form illustrated in FIG. 34), an identification of primary services form is transmitted to the healthcare service provider 120 in step 504 for identification by the healthcare service provider 120 of the primary type of service that he offers. An example of an identification of primary services form is illustrated in FIG. 35. This page contains a menu comprising a number of different types of healthcare service providers 120, such as a physician, dentist, physical therapist, etc. If the healthcare service provider 120 already has a profile stored in the healthcare service provider database 1300, the healthcare service provider's corresponding record is retrieved from the database 1300 and the previously selected service stored in field 1315 is identified for the healthcare service provider 120 in the form of a dot filled in the bubble corresponding to the service. The healthcare service provider's selection regarding his primary type of service is received in step 506.

If in step 508, it is determined that the healthcare service provider 120 is a physician, a background request form is transmitted to the healthcare service provider 120 requesting that the healthcare service provider 120 identify his educational and training background, board certifications, office location and hours, medical group partners, and UPIN number (i.e., provider identification number stored in field 1320) in step 510. An example of a background request form is illustrated in FIG. 36. If the healthcare service provider 120 already has a profile stored in the physician background database 1700, this information is retrieved from fields 1715 to 1735 of the healthcare service provider's existing record and displayed in the appropriate boxes for review and/or modification by the healthcare service provider 120. The healthcare service provider's background information is received and stored in the appropriate fields of a record in the physician background database 1700 in step 512.

Identification of Services Offered

In step 514, if it is determined that the healthcare service provider 120 has selected to identify his services (e.g., has selected the option "Identify Services Offered" of the healthcare service provider options form illustrated in FIG. 34), an identification of healthcare service categories form is transmitted to the healthcare service provider 120 in step 516 for identification by the healthcare service provider 120 of the categories of services that he offers. An example of an identification of healthcare service categories form where the healthcare service provider 120 has previously identified service categories (e.g., "CARDIOVASCULAR AND THORACIC SURGERY" and "PRIMARY CARE: INTERNAL MEDICINE") is illustrated in FIG. 37, and this information has been retrieved from field 1310 healthcare service provider database 1300 (from all records associated with the healthcare service provider 120 as identified by log-in identifier) and displayed for the healthcare service provider 120 in the appropriate fields of the form. The healthcare service provider 120 is provided with the options of selecting one of their previously identified service categories, adding a new category or deleting a category.

In step 518, it is determined whether the healthcare service provider 120 has selected to add a new service category, and if so, it is determined in step 520 whether the healthcare service provider 120 is a physician by reference to field 1315 of the healthcare service provider database 1300. If the healthcare service provider 120 is a physician, a list of physician services form is transmitted to the healthcare service provider 120 in step 522. An example of a list of physician services form is illustrated in FIG. 38. A listing of a number of physician specialties, such as "Allergy and Immunology", "Hand Surgery" and "Urology," are provided for selection by the healthcare service provider 120. A field is also provided for a beginning effective date for the selected specialty. The healthcare service provider's selection and the beginning effective date are received and stored in fields 1310 and 1325, respectively, of the healthcare service provider database 1300 in step 524.

If the healthcare service provider 120 is not a physician, a list of non-physician services form is transmitted to the healthcare service provider 120 in step 526. An example of a list of non-physician services form is illustrated in FIG. 39. A listing of a number of non-physician specialties, such as "Pharmacy" and "Social Worker" are provided for selection by the healthcare service provider 120. A field is also provided for a beginning effective date for the selected specialty. The healthcare service provider's selection and the beginning effective date are received and stored in fields 1310 and 1325, respectively, of the healthcare service provider database 1300 in step 528.

The service category will appear on the identification of healthcare service categories form and to the user 110 during the healthcare services panel selection process as of the beginning effective date.

If it is determined in step 530 that the healthcare service provider 120 would like to remove a service from the list of proffered services, the healthcare service provider 120 is required to indicate which service category to remove from his list of service categories by transmitting a service category removal form (not shown). A service category removal form is identical to the list of physician services form or list of non-physician services form illustrated in FIG. 38 or 39 (depending on whether the healthcare service provider 120 is a physician) with the exception of that it only lists the service categories for which the healthcare service provider has an active record in the healthcare service provider database 1300 (i.e., each category field 1310 for which the ending effective date is later than the current date) and that it requests the healthcare service provider to elect a service category to be deleted and an ending effective date for that service category. The selection is received from the healthcare service provider 120 and the ending effective date is stored in field 1330 of the appropriate record of the healthcare service provider database 1300 in step 532, and the process continues at step 516 with the transmission of an updated identification of service category form. The service category will appear on the identification of healthcare service categories form and to the user 110 during the healthcare services panel selection process until the ending effective date.

In step 534, once the services have been identified, a CPT code form is transmitted to the healthcare service provider 120 to identify the services included in the healthcare service providers rates by a Current Procedural Terminology ("CPT") code. CPT codes are the standard healthcare industry categorization for physician services and have been developed and copyrighted by the American Medical Association. An example of a CPT code form is illustrated in FIG. 40. Although not described herein in detail, the CPT code form preferably provides the healthcare service provider 120 with options to review standardized list(s) of CPT codes, add a standardized list of CPT codes, add or delete individual CPT codes or ranges of CPT codes, review a current list of CPT codes, effectuate date of changes or finalize the list. The selection of the CPT code(s) by the healthcare service provider 120 is received and stored in the appropriate field of the CPT database 1600 in step 536. For example, in record 1660, the physician "patch_adams" (provider ID #87654321) has chosen to include CPT 99211 (an Office/Outpatient visit for an established patient) in his covered services for PRIMARY CARE INTERNAL MEDICINE.

Identification of Rates

In step 538, if it is determined that the healthcare service provider 120 has selected to identify his rates (e.g., has selected the option "Review, Load or Update Your Rates" of the healthcare service provider options form illustrated in FIG. 34), an identification of healthcare service provider rates form is transmitted to the healthcare service provider 120 in step 540 for identification by the healthcare service provider 120 of the rates the healthcare service provider 120 charges for each category of service that he offers. An example of an identification of healthcare service provider rates form is illustrated in FIG. 41. This page contains a first menu comprising the categories of services that the healthcare service provider 120 offers, as retrieved from field 1310 of the healthcare service provider's records stored in the healthcare service provider database 1300, and a second menu comprising the options of "Pre-Paid" and "Fee-For-Service" for selection by the healthcare service provider 120 of the type of rate to be associated with the service category. The healthcare service provider's selection regarding the type of rate to be associated with the selected service category is received and stored in field 1335 of the healthcare service provider database 1300 in the record corresponding to the selected service category (by reference to field 1310) in step 542.

In step 544, if it is determined that that healthcare service provider 120 has selected the rates associated with the specific service category to be pre-paid, a pre-paid options form is transmitted to the healthcare service provider 120 in step 546. An example of a pre-paid options form is illustrated in FIG. 42. The pre-paid options form provides the healthcare service provider 120 with the options to: (1) review his current rates associated with a specific service category (step 548); (2) modify or load new rates to be charged for the specific service category (step 554); or (3) modify required notice of changes from patients (step 579).

In step 548, if it is determined that the healthcare service provider 120 would like to review his current rates, in step 550 the healthcare service providers records are retrieved from the rates database 1800 (as identified by log-in identifier) and the list of rates associated with the specific service category by age range corresponding to a monthly rate for males and a monthly rate for females are displayed for the healthcare service provider 120 in a chart format (not shown) in step 552.

If it is determined in step 554 that the healthcare service provider 120 would like to modify current rates or load new rates, a rates selection form is transmitted to the healthcare service provider 120 in step 556. An example of a rates selection form is illustrated in FIG. 43. The rates selection form provides the healthcare service provider 120 with the following options: (1) to enter new rates or modify individual rates; (2) to apply a single percentage adjustment to existing rates; and (3) to apply a dollar adjustment to rates. The option for rate selection chosen by the healthcare service provider 120 is received in step 558.

In step 560, if it is determined that the healthcare service provider 120 would like to enter new rates or modify individual rates (i.e., option (1) immediately above), a rates entry form is transmitted to the healthcare service provider 120 in step 562. An example of a rates entry form is illustrated in FIG. 44. The rates entry form provides the healthcare service provider 120 with the following options for rate entry: (1) to manually enter rates for each co-payment and age/gender category; (2) to create a set of percentage adjustment tables that will develop all rates by applying a percentage adjustment to the healthcare service providers chosen "standard" age/gender category; and (3) to view various adjustment tables that will assist the healthcare service provider 120 in establishing his rate tables. The selection for rate entry by the healthcare service provider 120 is received in step 564.

In step 566, if it is determined that the healthcare service provider 120 would like to manually enter his rates for each co-payment and age/gender category (i.e., option (1) immediately above), a rates determination form is transmitted to the healthcare service provider 120 in step 568. An example of a rates determination form is illustrated in FIG. 45. The rates determination form provides for entry by the healthcare service provider 120 of a co-payment and the monthly dollar rate for pre-paid services per consumer based on a patient's age (in five-year increments) and gender. The healthcare service provider 120 can identify individual age/gender combinations to which they do not want to offer rates and/or services by entering a zero in the appropriate age/gender cell. If the healthcare service provider 120 already has rates stored in an associated record in the rates database 1800, this information is retrieved and displayed for the healthcare service provider 120 in the appropriate fields of the rates determination form for modification or review by the healthcare service provider 120. The healthcare service provider's information is received from the healthcare service provider 120 and stored in the appropriate fields of the records associated with the healthcare service provider 120 (as identified by log-in identifier and age category) in the rates database 1800 in step 570.

In step 572, if it is determined that the healthcare service provider 120 would like to adjust his rates (i.e., options (2) & (3) immediately above), in step 574 a rate adjustment form (not shown) is transmitted requesting the healthcare service provider 120 to provide an adjustment percentage or dollar adjustment amount. This information is received and used to accordingly calculate new rates which are stored in fields 1825 and 1830 of the records associated with the healthcare service provider 120 (as identified by log-in identifier) in the rates database 1800 in step 576.

In step 573, if it is determined that the healthcare service provider 120 would like view various adjustment tables that will assist the healthcare service provider 120 in establishing his rate tables (i.e., option (3) above), information including average tables (including straight average, weighted average, and median ratio) and actuarial tables (e.g., from actuarial firms like Towers Perrin and M&R) is transmitted to the healthcare service provider 120 in step 578. This information can be, for example, stored as Web site pages at the central server 200, or be provided on the rate determination form as hyperlinks to Web sites containing this information. In a preferred embodiment, the healthcare service provider 120 can elect to automatically incorporate the data received in step 578 when establishing its rate tables.

In step 579, if it is determined that the healthcare service provider 120 would like to modify required notice of changes from patients, a notice requirement form is transmitted to the healthcare service provider 120 in step 580. An example of a notice requirement form is illustrated in FIG. 46. The notice requirement form provides for entry by the healthcare service provider 120 of a requirement as to how much advance notice it must receive to accept a new pre-paid patient. It provides for entry by the healthcare service provider 120 as to patients with pre-paid care and for patients without pre-paid care. The options for entry range from no notice to four months notice, in intervals of a month. This information is received from the healthcare service provider 120 and stored in the appropriate fields of the record(s) associated with the healthcare service provider 120 (as identified by log-in identifier) in the healthcare service provider database 1300 in step 582.

The healthcare service provider registration process ends in step 584.

Identification of Referrals

Figure 6B:
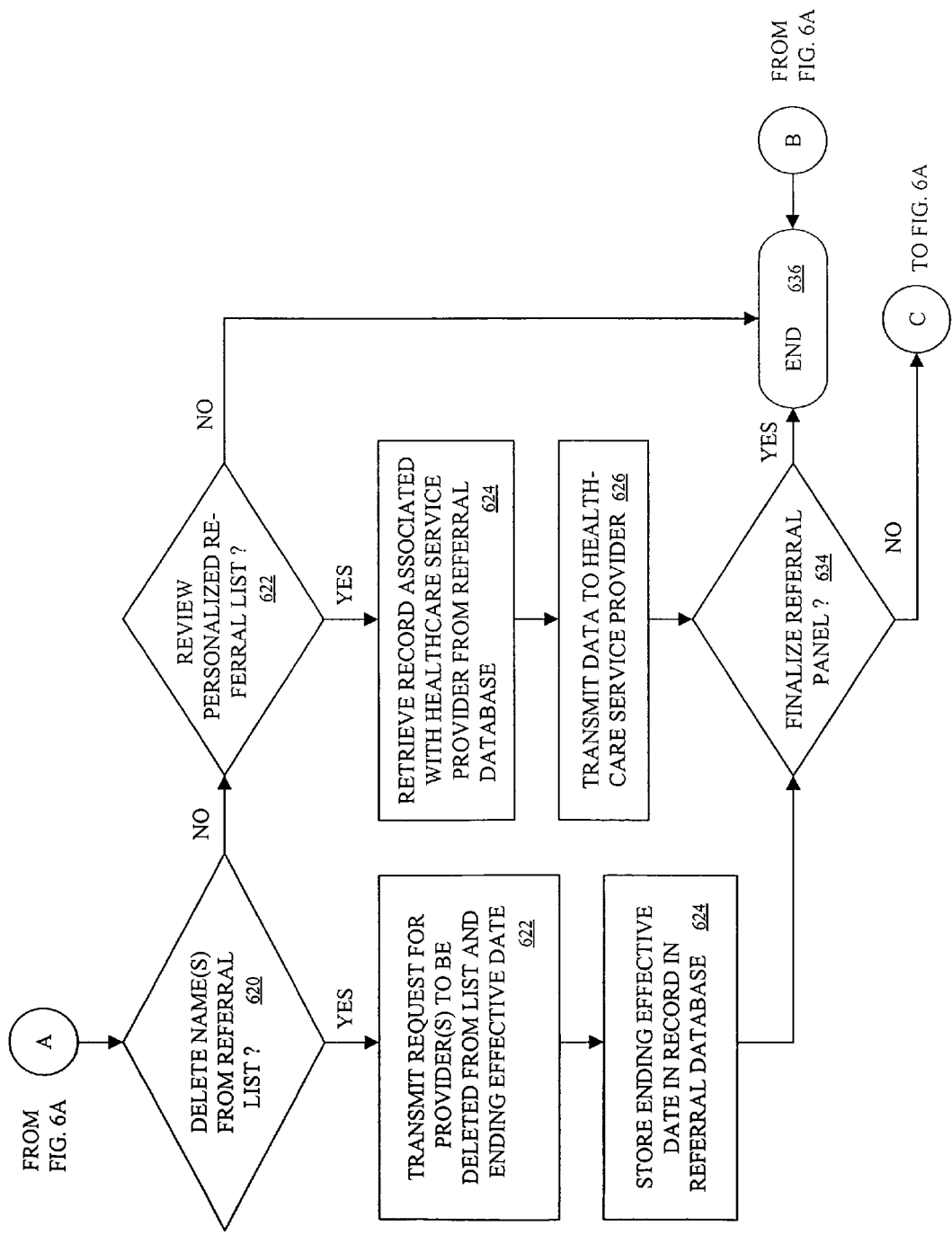

Referring now to FIGS. 6A-6B, a healthcare service provider referrals process begins in step 600.

In step 602, a referrals form is transmitted to the healthcare service provider 120 for the healthcare service provider 120 to identify the list of physicians, hospitals and other healthcare providers that the healthcare service provider 120 wishes to include in his referral panel and to whom he may refer his patients. An example of a referrals form is illustrated in FIG. 47. The healthcare service provider 120 is provided with the following options: (1) to review standardized panels; (2) to add a standardized referral panel; (3) to add individual physicians, hospitals or other healthcare service providers; (4) to delete individual physicians, hospitals or other healthcare service providers; (5) to review his personalized referral panel; and (6) to finalize his personalized referral panel. The selection by the healthcare service provider 120 is received in step 604.

In step 606, if it is determined that the healthcare service provider 120 would like to view standardized panels or a referral panel of one of his peers (i.e, option (1) immediately above), this information is transmitted to the healthcare service provider 120 in step 608. This information can be, for example, stored as Web site pages at the central server 200, or be provided on the referrals form as hyperlinks to Web sites containing this information. Third party entities, such as a Physician Hospital Organization ("PHO") or an Independent Practice Association ("IPA") may choose to establish standardized panels in order to assist physicians in developing their referral panel. However, to be displayed to the user 110 as a referred provider during the healthcare services panel registration process, each referred healthcare service provider 120 must be registered with the system and assigned a provider identifier.

In step 610, if it is determined that the healthcare service provider 120 would like to add a standardized referral panel (i.e., option (2) above), the panel (including healthcare service provider names/categories) is retrieved from the source(s) described above and each panel provider name, category and provider identification number is stored in fields 1925, 1920 and 1930, respectively, of separate records associated with the healthcare service provider 120 (as identified by log-in identifier and referrer provider identification number) in the referral database 1900 in step 612. Each record is assigned the same unique panel identifier, which is stored in field 1935.

In step 614, if it is determined that the healthcare service provider 120 would like to add individual physicians, hospitals, or other healthcare service providers to his referral panel (i.e., option (3) immediately above), in step 616 the healthcare service provider 120 is transmitted a referral addition request form (not shown) requesting the healthcare service provider 120 to transmit the names, provider identification numbers, categories and beginning effective dates of the referred healthcare service providers to be added to his referral list. This information is received and stored in fields 1925, 1930, 1920, and 1910, respectively, of separate records (per referred healthcare service provider/category combination) associated with the healthcare service provider 120 (as identified by log-in identifier and referrer provider identification number) of the referral database 1900 in step 618.

If it is determined in step 620 that the healthcare service provider 120 would like to delete individual physicians, hospitals, or other healthcare service providers from his referral list (i.e., option (4) immediately above), in step 622 the healthcare service provider 120 is transmitted a referral deletion request form (not shown) requesting the healthcare service provider 120 to transmit the identification of the healthcare service provider(s) to be deleted from his referral list (by name(s) and categories of service) and the ending effective date(s) of referral. This information is received and the name(s) are "deleted" by identifying the record(s) of the referred healthcare service provider (by reference to the healthcare service provider's log-in identifier in field 1905 and the referred provider's name(s) in field 1925 of the referral database 1900) and storing the ending effective date(s) in field 1920 in step 624. The referred healthcare service provider's name will be displayed to the user 110 during the healthcare services panel selection process (if the referring healthcare service provider 120 is chosen as the user's Primary Physician) until the ending effective date, at which time it will be effectively "deleted".

In step 622, if it is determined that the healthcare service provider 120 has selected to review his personalized referral panel (i.e., option (5) immediately above), all of the records associated with the healthcare service provider 120 (as identified by log-in identifier and provider identification number) of the referral database 1900 for which the current date is greater than the beginning effective date in field 1910 and less than the ending effective date in field 1915 are retrieved and the data is transmitted to the healthcare service provider 120 in chart form (not shown) in step 626.

In step 634, if it is determined that the healthcare service provider 120 has selected to finalize his personalized referral panel (i.e., option (6) immediately above), the process ends in step 636.

Information Retrieval Process

Figure 7A:
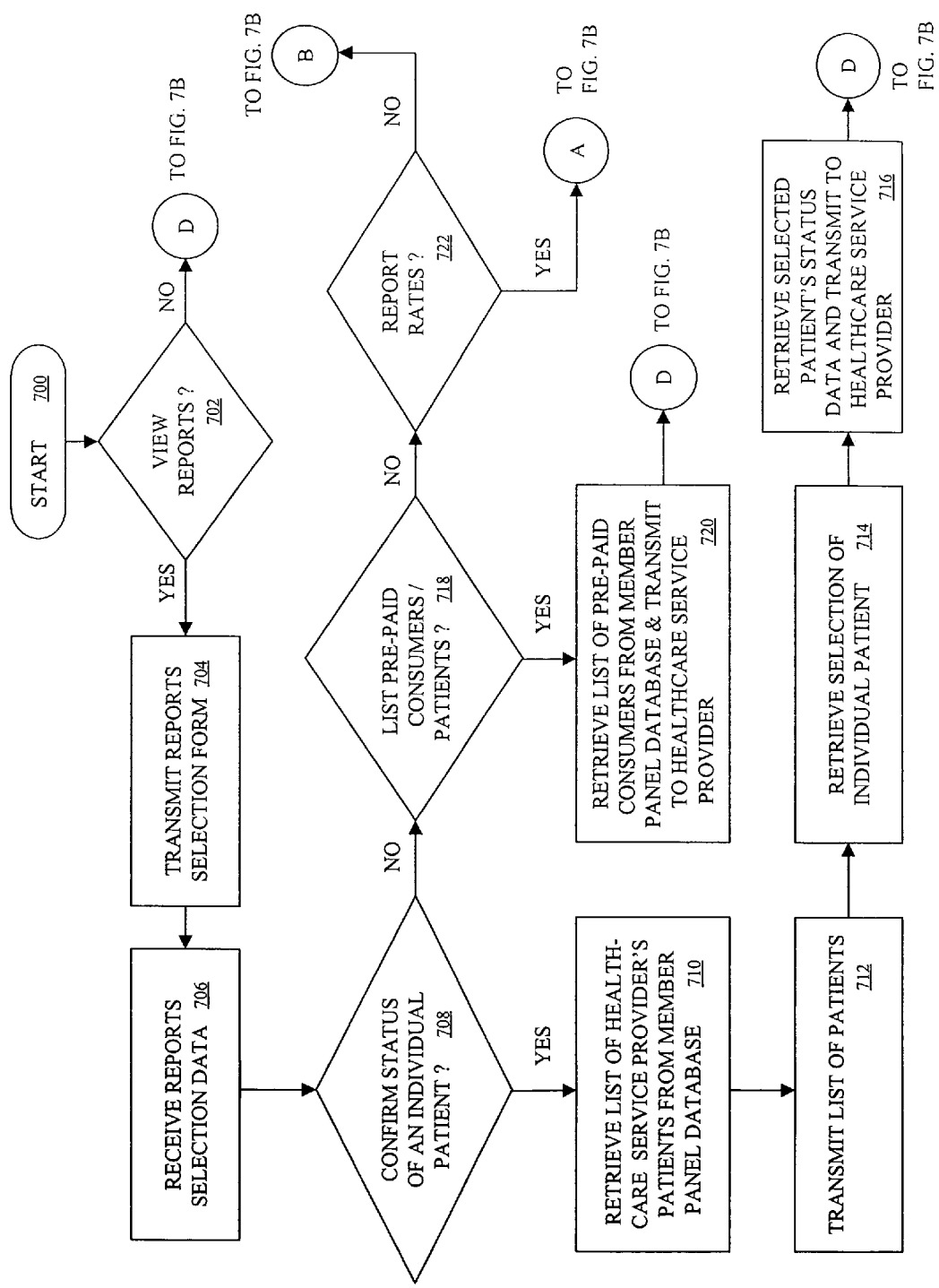
FIGS. 7A-7B are flow diagrams illustrating an embodiment of a healthcare service provider information retrieval process.
Figure 7B:
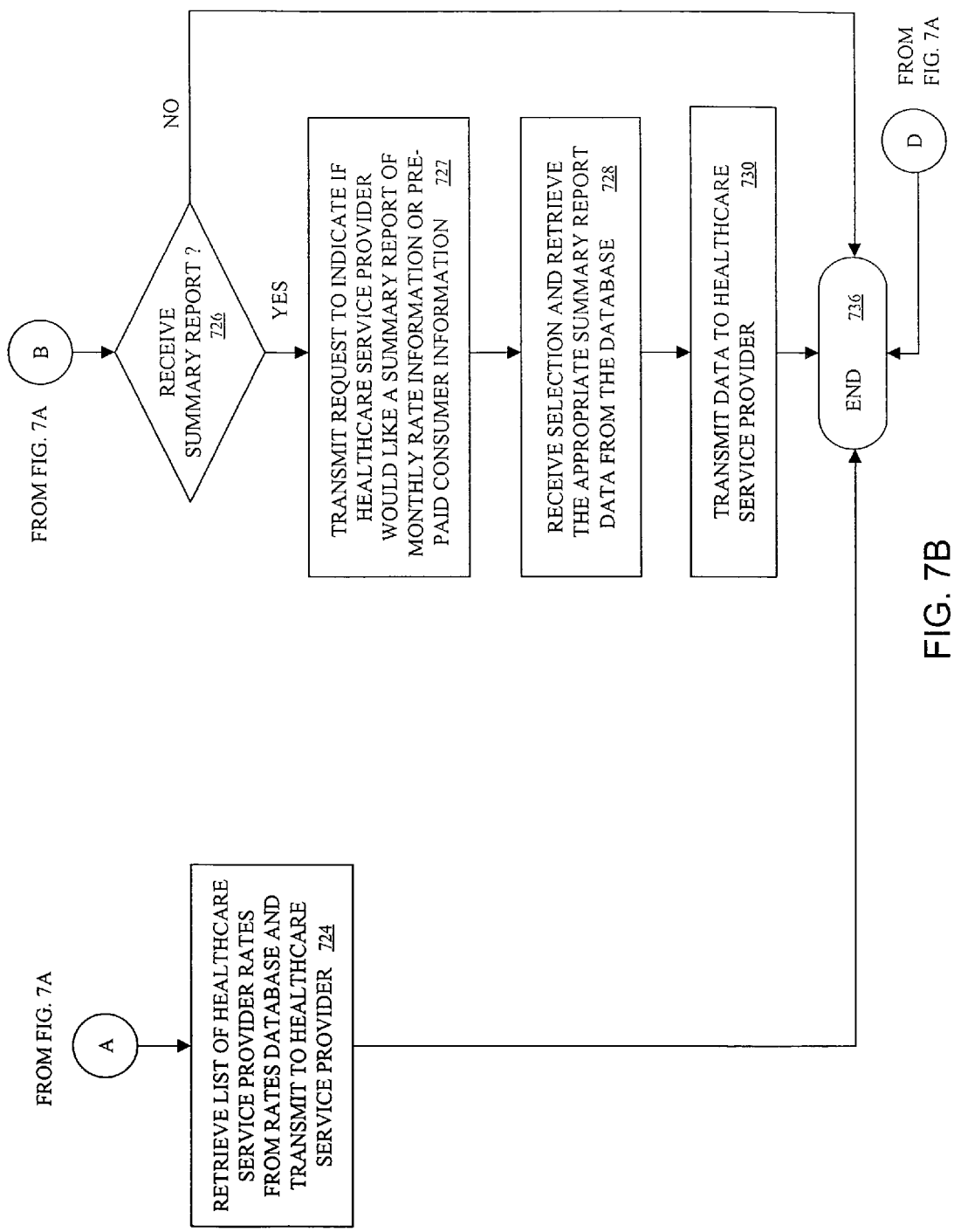

Referring now to FIGS. 7A-7B, a healthcare service provider information retrieval process begins in step 700.

In step 702, if it is determined that the healthcare service provider 120 would like to view reports, a reports selection form is transmitted to the healthcare service provider 120 in step 704. An example of a reports selection form is illustrated in FIG. 48. The reports selection form provides the healthcare service provider 120 with the options of: (1) confirming the status of an individual patient; (2) receiving a list of pre-paid consumers/patients; (3) receiving a rates report; and (4) receiving summary reports. The healthcare service provider's selection is received in step 706.

In step 708, if it is determined that the healthcare service provider 120 would like to confirm the status of and individual patient, a list of names of the healthcare service provider's patients are retrieved in step 710 from field 907 of associated records of the member panel database 900 (by reference to the healthcare service provider's provider identification number stored in field 915) and transmitted to the healthcare service provider 120 in step 712 for selection by the healthcare service provider 120. In step 714, the selected patient's record is retrieved from the member panel database 900 and the information contained therein (i.e., "status data") is transmitted to the healthcare service provider 120 in chart form (not shown) in step 716.

In step 718, if it is determined that the healthcare service provider 120 would like a listing of his pre-paid consumers/patients, a list of names of the healthcare service provider's pre-paid consumers/patients are retrieved from field 907 of associated records of the member panel database 900 (by reference to the healthcare service provider's provider identification number stored in field 915 and the presence of a "P" in field 923) and transmitted to the healthcare service provider 120 in chart form (not shown) in step 720.

In step 722, if it is determined that the healthcare service provider 120 has selected to receive a rates report, in step 724 a list of the healthcare service provider's rates are retrieved from the rates database 1800 and transmitted to healthcare service provider 120 in the same manner described above with respect to the rates identification form.

In step 726, if it is determined that the healthcare service provider 120 has selected to receive a summary report, in step 727 the healthcare service provider 120 is requested to indicate if he would like a summary report of monthly rate information (by age/gender/co-payment, age/gender or co-payment), or pre-paid consumer information (by age/gender/co-payment, age/gender or co-payment). Upon receipt of the selection by the healthcare service provider 120, the record(s) associated with the healthcare service provider 120 are retrieved from the member panel database 900 (by reference to the provider identification number stored in field 915) and an appropriate summary report data Is generated in step 728 and transmitted to the healthcare service provider 120 in chart form (not shown) in step 730.

The information retrieval process ends in step 736.

Sponsor Options Process

Figure 8B:
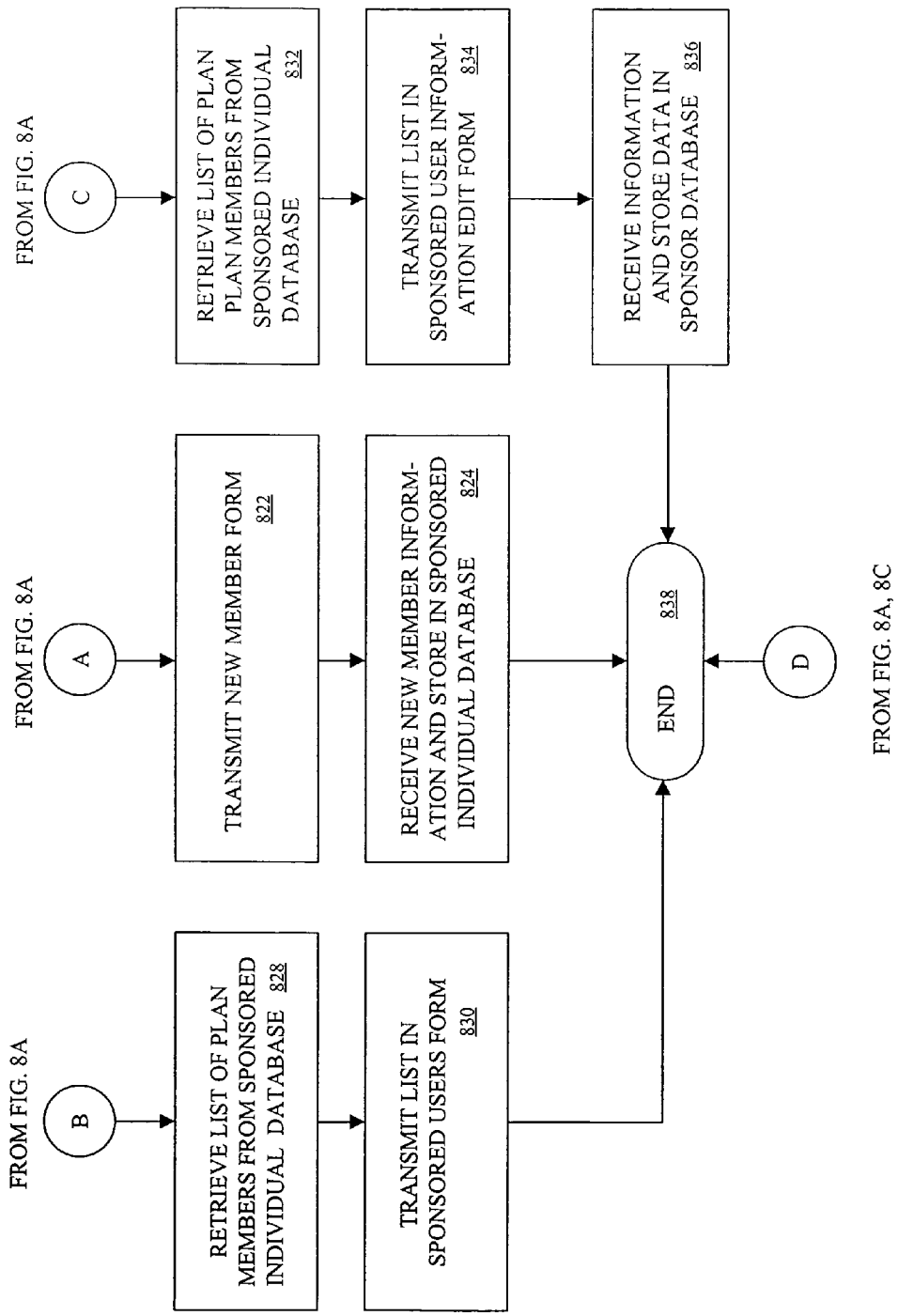

The sponsor registration process will now be described with reference to FIGS. 8A-8C.

If in step 350 (described above with respect to the user registration process) it is determined that the registrant is a "sponsor," i.e., the entity/individual responsible for paying for all or part of the user's healthcare costs, the sponsor registration process begins at step 800, and a sponsor option request form is transmitted to the sponsor 130 in step 802. An example of a sponsor option request form is illustrated in FIG. 49. Generally, the sponsor 130 is offered the following options: (1) to create or update his profile information; (2) to generate reports; and (3) to add, review, or edit his list of sponsored plan members and the amount of benefit that the sponsor 130 contributes to a plan member's health plan. The sponsor's selection is received in step 804.

In step 806, if it is determined that the sponsor 130 has selected to create or edit his profile (e.g., has selected the option "Profile Information" of the sponsor request form of FIG. 49), it is determined in step 808 whether the sponsor 130 has previously registered his profile in the sponsor information database 1400 (as identified by the sponsor's log-in identifier stored in field 1405). If the sponsor 130 already has a profile stored in the sponsor information database 1400, the sponsor's record is retrieved from the sponsor information database 1400 in step 810. In step 812, the information is transmitted to the sponsor 130 in the appropriate fields of a sponsor profile form (described below) to allow the sponsor 130 to make any necessary changes to the existing data.

If in step 808, it is determined that the sponsor 130 does not have a profile stored in the sponsor information database 1400, a blank sponsor profile form is transmitted to the sponsor 130 in step 814 and the sponsor profile information is received and stored in the appropriate fields of the sponsor information database 1400 in step 815. An example of a sponsor profile form is illustrated in FIG. 50, requesting that the sponsor 130 provide its name, address, contact name, contact phone number, the type of sponsor it is (employer/insurer/other), and a sponsor identification code for identification purposes. In a preferred embodiment, the sponsor registration form will also provide a field for the sponsor 130 to enter a bank account number (and an associated ABA number) if the sponsor 130 elects to have the costs of sponsored member plans directly paid from a listed bank account.

In step 807, if it is determined that the sponsor 130 has selected to generate reports (i.e., has selected the option "Generate Reports" of the sponsor option page illustrated in FIG. 49), a sponsor report selection form is transmitted to the sponsor 120 in step 842 requesting the sponsor 130 to identify what type of report is to be generated. An example of a sponsor report selection form is illustrated in FIG. 54. Generally, the sponsor report selection form allows the sponsor 130 to select a customized report based on either its plan members (e.g., by geographic area) or its aggregated or detailed contribution amounts (e.g., by month). The sponsor's report selection is received in step 844.

In step 846, the records of the sponsored individual database 1500 associated with the sponsor (as identified by the sponsor identification code stored in field 1505), the records of the sponsoree database 1100 associated with the sponsor (as identified by the sponsor identification code stored in field 1125) and the records of the member panel database 900 associated with the sponsor (as identified by the member identifier stored in field 905, which is linked to the member identifier 1211 of the member demographics database 1200 in order to identify the sponsoree identifier 1240 of the member demographics database 1200, which is linked to the sponsoree identifier 1515 of the sponsored individual database 1500 in order to identify the sponsor identification code 1505 of the sponsored individual database 1500) are retrieved and a report is generated in accordance with the sponsor's selection and the data contained in the retrieved record(s). The generated report(s) are transmitted in chart form (not shown) to the sponsor 130 in step 848.

In step 816, if it is determined that the sponsor 130 has selected to enter sponsorship data for a new member (i.e., has selected the option "Add a New Plan Member" on the sponsor option page illustrated in FIG. 49), a new member form is transmitted to the sponsor 130 in step 822. An example of a new member form is illustrated in FIG. 52. Generally, the new member form provides fields for the sponsor 130 to identify the sponsoree's name, sponsor contribution, sub-sponsor identification code, sponsoree identification code, and initial sponsoree password. The new member sponsorship information is received and information regarding each new plan member is stored in the appropriate fields of its own separate record of the sponsored individual database 1500 in step 824.

In a preferred embodiment, the information received in step 824 can be received in electronic format using a predetermined data record layout.

In step 818, if it is determined that the sponsor 130 has selected to review its list of sponsored members (i.e., has selected the option "Review Plan Members" on the sponsor option page illustrated in FIG. 49), in step 828 a list of names of the members for whom the sponsor 130 is responsible for payments is generated by reference to fields 1505 and 1520 of the sponsored individual database 1500. The list of sponsored members is then transmitted to the sponsor 130 in a sponsored members form in step 830. An example of a sponsored members form for Wizig&Company is illustrated in FIG. 51. The sponsored members form also contains fields listing the additional data stored in each field of the sponsored individual database 1500, such as sponsoree identifier (field 1515), contribution amount (field 1525) and initial password (field 1530).

In a preferred embodiment, the form lists the names of the members in hyperlink format to provide the sponsor 130 with the option of double-clicking on a member's name to remove the member from the list or to retrieve the member's profile, in which case the member's profile is retrieved from the sponsored individual database 1500 and displayed in the appropriate fields of a new member form (discussed below) to allow the sponsor 130 to make any necessary changes to the existing data.

In step 820, if it is determined that the sponsor 130 has selected to edit its list of sponsored members (i.e., has selected the option "Edit Plan Members" on the sponsor option page illustrated in FIG. 49), in step 832 a list of names of the members for whom the sponsor 130 is responsible for payments is generated by reference to fields 1505 and 1520 of the sponsored individual database 1500. In step 834, the information is transmitted to the sponsor 130 in a user information edit form to allow the sponsor 130 to view and/or make changes to the existing data. An example of a user information edit form for Wizig&Company is illustrated in FIG. 53. In step 836, the member sponsorship information is received and stored in the sponsored individual database 1500 in the appropriate record(s) associated with sponsor 130.

The sponsor registration process ends in step 838.

In a preferred embodiment, the healthcare service providers 120 and the sponsors 130 are provided with the option to purchase banner advertisements to be displayed to users over the Internet 140 based on predetermined criteria. These criteria include, for example: the broadcast region affected by the advertisement (e.g., national, regional, or only within a specified distance from a ZIP code, such as closest, within 5 miles, within 10 miles, within 15 miles, within 20 miles, or within 25 miles); the size of advertisement; the frequency with which the advertisement will run; the time of day that the advertisement will run; the time duration of the advertisement; the demographics of users targeted by the advertisement; the Web page(s) on which the advertisement will run; the cost to run the advertisement; whether the advertisement is new or has previously been run; and the method of payment used to pay for the disbursement of the advertising (e.g., online or invoice).

In another preferred embodiment, the user 110 is provided with a comment form which allows the user 110 to make a comment about a healthcare service provider 120, the comment being stored and accessible to other users. The healthcare service provider 120 is also preferably provided with an opportunity to respond to comments made about it by users, the response being stored and accessible to users.

It is to be understood that the embodiments and variations shown and described herein are merely illustrative of the principle of this invention and that various modifications may be implemented by those skilled in the art without departing from the scope and spirit of the invention.

I claim:

1. A computer-system implemented method for providing a user with a customized healthcare services insurance package, comprising:

receiving a personal information data regarding a user, wherein the personal information data comprises a user identifier and an uncredited umbrella policy cost;

forwarding information regarding a plurality of healthcare service providers wherein each healthcare service provider is associated with an individual cost and an umbrella policy credit;

receiving a selection of a healthcare services panel comprising a user-defined co-pay amount selected from a provider co-pay range and at least one of the healthcare service providers;

aggregating the costs of healthcare service providers on the healthcare services panel;

aggregating the umbrella policy credits of each healthcare service provider on the healthcare services panel;

using said computer system to calculate a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost; and forwarding a description of the determined healthcare services insurance package, said description including a proposed periodic payment for purchasing said determined healthcare services insurance package.

2. The method of claim 1, wherein each healthcare service provider is associated with an individual cost and an umbrella policy credit and the personal information data further comprises an uncredited umbrella policy cost and an identification of a plurality of individuals to be associated with the healthcare services insurance package and wherein determining the healthcare services package further comprises:

aggregating the individual costs of each healthcare service provider on the healthcare services panel of each of the plurality of individuals;

aggregating the umbrella policy credits of each healthcare service provider on the healthcare services panel of each of the plurality of individuals;

calculating a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost.

3. The method of claim 2, wherein the personal information data further comprises an amount of deductible on an umbrella policy, and wherein determining the healthcare services package is further based on the amount of deductible.

4. The method of claim 3, wherein the personal information data further comprises an amount of deductible on an umbrella policy for each individual, and wherein determining the healthcare services insurance package is further based on the amounts of deductible.

5. A computerized system for providing a user with a customized healthcare services insurance package, comprising:

a memory device; and a processor disposed in communication with said memory device, said processor configured for:

receiving a personal information data regarding a user, wherein the personal information data comprises a user identifier and an uncredited umbrella policy cost;

forwarding information regarding a plurality of healthcare service providers, wherein each healthcare service provider is associated with an individual cost and an umbrella policy credit;

receiving a selection of a healthcare services panel comprising a user-defined co-pay amount selected from a provider co-pay range and at least one of the healthcare service providers;

aggregating the costs of healthcare service providers on the healthcare services panel;

aggregating the umbrella policy credits of each healthcare service provider on the healthcare services panel;

calculating a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost; and forwarding a description of the determined healthcare services insurance package, said description including a proposed periodic payment for purchasing said determined healthcare services insurance package.

6. The system of claim 5, wherein each healthcare service provider is associated with an individual cost and an umbrella policy credit and the personal information data further comprises an uncredited umbrella policy cost and an identification of a plurality of individuals to be associated with the healthcare services insurance package, and wherein determining the healthcare services package further comprises:

aggregating the individual costs of each healthcare service provider on the healthcare services panel of each of the plurality of individuals;

aggregating the umbrella policy credits of each healthcare service provider on the healthcare services panel of each of the plurality of individuals;

calculating a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost.

7. The system of claim 6, wherein the personal information data further comprises an amount of deductible on an umbrella policy, and wherein determining the healthcare services package is further based on the amount of deductible.

8. The system of claim 7, wherein the personal information data further comprises an amount of deductible on an umbrella policy for each individual, and wherein determining the healthcare services insurance package is further based on the amounts of deductible.

9. A processor-readable medium storing processor readable instructions for providing a user with a customized healthcare services insurance package, comprising:

processor readable instructions are issuable by a processor for:

receiving a personal information data regarding a user, wherein the personal information data comprises a user identifier and an uncredited umbrella policy cost;

forwarding information regarding a plurality of healthcare service providers, wherein each healthcare service provider is associated with an individual cost and an umbrella policy credit;

receiving a selection of a healthcare services panel comprising a user-defined co-pay amount selected from a provider co-pay range and at least one of the healthcare service providers;

aggregating the costs of healthcare service providers on the healthcare services panel;

aggregating the umbrella policy credits of each healthcare service provider on the healthcare services panel;

calculating a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost; and forwarding a description of the determined healthcare services insurance package, said description including a proposed periodic payment for purchasing said determined healthcare services insurance package.

10. The medium of claim 9 wherein each healthcare service provider is associated with an individual cost and an umbrella policy credit and the personal information data further comprises an uncredited umbrella policy cost and an identification of a plurality of individuals to be associated with the healthcare services insurance package, and further comprising:

aggregating the individual costs of each healthcare service provider on the healthcare services panel of each of the plurality of individuals;

aggregating the umbrella policy credits of each healthcare service provider on the healthcare services panel of each of the plurality of individuals;

calculating a difference between the uncredited umbrella policy cost and the aggregated amount of umbrella policy credits, wherein the difference represents a credited umbrella policy cost; and determining the healthcare services insurance package based on a sum of the aggregated costs and the credited umbrella policy cost.

11. The medium of claim 10, wherein the personal information data further comprises an amount of deductible on an umbrella policy, and wherein determining the healthcare services package is further based on the amount of deductible.

12. The medium of claim 11, wherein the personal information data further comprises an amount of deductible on an umbrella policy for each individual, and wherein determining the healthcare services insurance package is further based on the amounts of deductible.

* * * * *